(12) United States Patent
Natrajan

(10) Patent No.: US 12,234,209 B2
(45) Date of Patent: *Feb. 25, 2025

(54) N-ALKYLATION OF ACRIDANS

(71) Applicant: Siemens Healthcare Diagnostics Inc., Tarrytown, NY (US)

(72) Inventor: Anand Natrajan, Manchester, NH (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 484 days.

This patent is subject to a terminal disclaimer.

(21) Appl. No.: 17/454,916

(22) Filed: Nov. 15, 2021

(65) Prior Publication Data

US 2022/0073468 A1 Mar. 10, 2022

Related U.S. Application Data

(63) Continuation of application No. 17/250,131, filed as application No. PCT/US2019/038955 on Jun. 25, 2019, now Pat. No. 11,203,573.

(60) Provisional application No. 62/689,811, filed on Jun. 25, 2018.

(51) Int. Cl.
C07D 219/06 (2006.01)

(52) U.S. Cl.
CPC .................................. *C07D 219/06* (2013.01)

(58) Field of Classification Search
CPC .................................................. C07D 219/06
See application file for complete search history.

(56) References Cited

U.S. PATENT DOCUMENTS

| | | | |
|---|---|---|---|
| 5,468,646 A | 11/1995 | Mattingly et al. | |
| 5,656,426 A | 8/1997 | Law et al. | |
| 6,664,043 B2 | 12/2003 | Natrajan et al. | |
| 7,309,615 B2 | 12/2007 | Natrajan et al. | |
| 7,459,284 B2 | 12/2008 | Jiang et al. | |
| 7,875,467 B2 * | 1/2011 | Natrajan | C07D 219/04 |
| | | | 435/7.1 |
| 8,293,908 B2 * | 10/2012 | Natrajan | C07D 219/04 |
| | | | 546/102 |
| 8,778,624 B2 | 7/2014 | Natrajan et al. | |
| 9,512,080 B2 * | 12/2016 | Natrajan | C07D 219/04 |
| 9,647,294 B2 | 5/2017 | Abe et al. | |
| 11,203,573 B2 * | 12/2021 | Natrajan | C07D 219/06 |
| 2015/0197491 A1 | 7/2015 | Natrajan et al. | |

FOREIGN PATENT DOCUMENTS

CN 102762539 10/2012

OTHER PUBLICATIONS

Natrajan, Green Hem, 2011, vol. 13, 913-921. (Year: 2011).*
Wang, RSC Adv., 2015, vol. 5 19989-20002. (Year: 2015).*
Adamczyk, Bioorg & Med Chem Lett, VOl 14, 2004, 3917-3921. (Year: 2004).*
Adamczyk et al., Neopentyl 3-Triflloxypropanesulfonate. A Reactive Sulfopropylation Reagent for the Preparation of Chemiluminescent Labels, J. Org. Chem. vol. 63, No. 16, Jul. 7, 1998, pp. 5636-5639.
International Search Report for PCT/US2019/038955 dated Oct. 21, 2019.
Atrajan, Anand et al: "Synthesis and properties of differently charged chemiluminescent acridinium ester labels"; Org. Biomol. Chem.; vol. 11; No. 6; (2013); pp. 1026-1039.
Avitabile, Barbara et al.: "Pentafluorophenyl Sulfonate Ester as a Protecting Group for the Preparation of Biaryl- and Heterobiaryl Sulfonate Esters"; Org. Lett.; vol. 7; No. 5;(2005) pp. 843-846.
Natrajan, Anand et al: "A comparison of chemiluminescent acridinium dimethylphenyl ester labels with different conjugation sites"; Org. Biomol. Chem.; vol. 13; No. 9; (2015); pp. 2622-2633.
Wang, Shenliang et al: "Synthesis and properties of chemiluminescent acridinium esters wit different N-alkyl groups"; RSC Adv.; vol. 5, No. 26; (2015), pp. 19989-20002.
Natrajan, A.; Sharpe, D.; Wen, D. "Effect of Surfactants On the Chemiluminescence of Acridinium Dimethylphenyl Ester Labels and Their Conjugates" Org Biomol Chem, (2011), vol. 9, 5092-5103.
Natrajan, A.; Sharpe, D.; Costello, J.; Jiang, Q. P. "Enhanced Immunoassay Sensitivity Using Chemiluminescent Acridinium Esters with Increased Light Output" Ann Biochem, (2010), vol. 406, 204-213.
Law et al., J., Novel Poly-substituted Aryl Acridinium Esters and their Use in Immunoassay, Biolumin. Chemilumin. 4 (1989): 88-98.
Bolt and Golka, Carcinogenicity categorization of chemicals-new aspects to be considered in a European perspective, Toxicol. Lett. 151 (2004): 251-254.
Ulland B, et al.,. Carcinogenicity of industrial chemicals propylene imine and propane sultone. Nature. 1971, vol. 230 (5294):460-461.
Natrajan and Wen, Facile N-alkylation of acridine esters with 1,3-propane sultone in ionic liquids, Green Chem. 13 (2011): 913-921.
Natrajan and Wen, A green synthesis of chemiluminescent N-sulfopropyl acridinium esters in ionic liquids without using the carcinogen 1, 3-propane sultone, Green Chem. Lett. Rev. 6 (2013): 237-248.
Greene, Theodora W.: "Protective groups in organic synthesis"; 3rd Ed.; pp. 451-452; protection of sulfonic acid.
Pauff SM, Miller SC. A trifluoroacetic acid-labile sulfonate protecting group and its use in the synthesis of a near-IR fluorophore. The Journal of Organic Chemistry. Jan. 2013;78(2):711-716.
Miller SC. Profiling sulfonate ester stability: identification of complementary protecting groups for sulfonates. J Org Chem. Jul. 2, 2010;75(13):4632-5.

(Continued)

*Primary Examiner* — D Margaret M Seaman

(57) ABSTRACT

The present invention provides compounds used in the synthesis of chemiluminescent acridinium compounds and methods of producing these compounds. Specifically, methods are provided for the N-alkylation of acridan compounds using alkylating reagents. Typically, these alkylating reagents comprise a protected sulfonate group protected with an acid-labile protecting group.

20 Claims, 2 Drawing Sheets

(56) References Cited

OTHER PUBLICATIONS

Natrajan et al., Chemiluminescence from alkoxy-substituted acridinium dimethylphenyl ester labels, Org. Biomol. Chem., 2012, 10, 3432-3447.
Natrajan and Sharpe, Synthesis and properties of differently charged chemiluminescent acridinium ester labels, Org. Biomol. Chem., 2013, 11, 1026-1039.

* cited by examiner

N-ALKYLATION OF ACRIDANS

CROSS-REFERENCE TO RELATED APPLICATION

This application claims priority of U.S. Provisional Application No. 62/689,811 filed Jun. 25, 2018, which is incorporated by reference herein in its entirety.

FIELD OF INVENTION

The present invention describes the synthesis of N-alkylated acridan compounds used in the synthesis of high light yield chemiluminescent acridinium compounds without using the carcinogenic chemical 1,3-propane sultone. The current process is also expected to be generally applicable for the synthesis of other chemiluminescent acridinium compounds containing functionalized N-alkyl groups at the acridinium nitrogen.

BACKGROUND OF INVENTION

Chemiluminescent acridininum labels are widely used in automated immunoassays. These labels exhibit excellent chemiluminescent stability compared to unsubstituted acridinium phenyl esters or acridinium sulfonamides (Law et al, *J. Biolumin. Chemilumin.* 4 (1989): 88-98; U.S. Pat. No. 8,778,624). Acridinium labels containing N-sulfopropyl groups are hydrophilic and display improved aqueous solubility compared to the corresponding N-methyl analogs (Law et al.; U.S. Pat. No. 5,656,426). These chemiluminescent labels also have low non-specific binding which can be further alleviated by the incorporation of poly(ethylene) glycol (PEG) or zwitterions in the acridinium ester structure (Natrajan et al, *Org. Biomol. Chem.* 9 (2011): 5092-5103; Natrajan et al, *Anal. Biochem.* 406 (2010): 204-213; U.S. Pat. No. 6,664,043).

The synthesis of acridinium labels containing N-sulfopropyl groups is ordinarily accomplished by N-alkylation of the acridine precurors with the reagent 1,3-propane sultone at high temperatures in neat reactions where the alkylating reagent is also the solvent (Law et al, U.S. Pat. No. 5,656,426). These harsh conditions for the N-alkylation reaction are necessitated by the poor reactivity of the hindered acridine nitrogen towards alkylating reagents. Although the neat reaction can be used for preparative purposes, a major disadvantage is that 1,3-propane sultone is quite toxic and poses a significant health hazard (Bolt and Golka, *Toxicol. Lett.* 151 (2004): 251-254; Ulland et al, *Nature* 230 (1971): 460-461). A synthetic protocol for the N-alkylation of acridine compounds in ionic liquids with substantially reduced quantities of 1,3-propane sultone compared to the neat alkylation reactions has also been developed (Natrajan and Wen, *Green Chem.* 13 (2011): 913-921; U.S. Pat. No. 8,293,908). The increased reactivity of the acridine precursors with 1,3-propane sultone in ionic liquids also enabled the synthesis of a variety of functionalized acridinium compounds (e.g., acridinium esters or acridinium sulfonamides) containing N-sulfopropyl groups with minimal side reactions or decomposition. Additionally, the synthesis of unsubstituted acridinium compounds (i.e., wherein C2-C8 carbon positions in the acridinium ring are each unsubstituted), can also be accomplished by N-alkylation of the corresponding acridan with the reagent sodium 3-bromopropane sulfonate in ionic liquids (U.S. Pat. No. 9,512,080; Natrajan and Wen, *Green Chem. Lett. Rev.* 6 (2013): 237-248). The acridan N-alkylation process eliminates the use of 1,3-propane sultone for the synthesis of unsubstituted N-sulfopropyl acridinium esters.

Unfortunately, these processes are not suited for the synthesis of electron-rich acridinium compounds. For example, electron-rich acridan precursors of these acridinium compounds are easily oxidized to their acridine counterpart when heated with sodium 3-bromopropane sulfonate in ionic liquids. As can be seen in synthetic schema (S1), the electron-rich acridans undergo oxidation to acridine rather than N-alkylation of the central ring nitrogen of the acridan system (i.e., N-alkylacridan is not formed). In synthetic schema S1, the acridan is electron-rich due to the presence of OR and R' groups at the C-2 and C7 positions of the acridan ring system.

(S1)

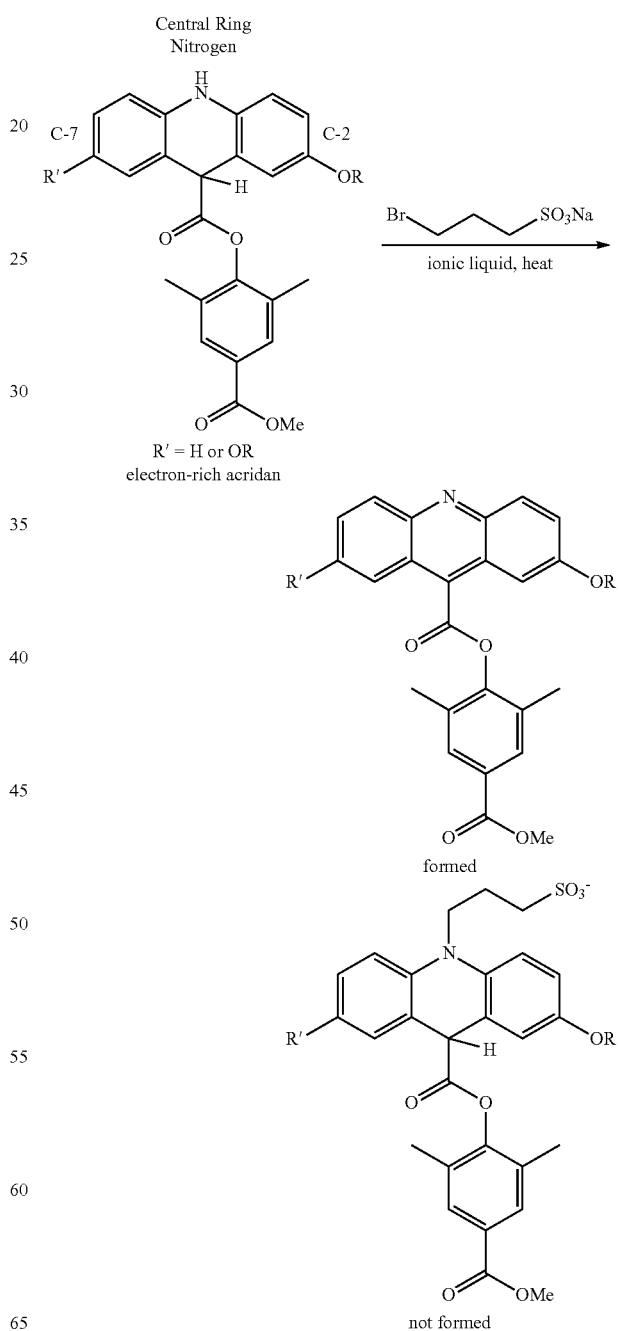

It is therefore an object of the invention to provide methods of producing N-alkylated acridine compounds unencumbered by these limitations.

SUMMARY

The present invention is partially premised on the discovery that electron-rich acridans (e.g., acridans containing one or two alkoxy groups at C-2 and/or C-7 of the acridan ring) can be alkylated with powerful alkylating reagents such as trifluoromethanesulfonates (triflates). These electron-rich acridans are acridan compounds having an electron density greater than the electron density of the same acridan in which the carbons at each of the C(1)-C(8) carbons of the acridan ring are bound to hydrogen. For example, the electron-rich acridan may have the structure of formula (A1):

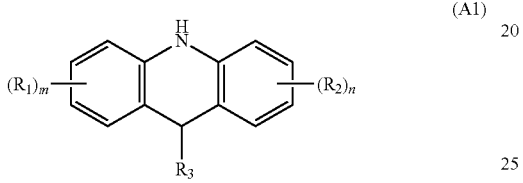

wherein "m" and "n" are independently 0-4 (i.e., 0, 1, 2, 3, or 4) and at least one of "m" or "n" is greater than 0;

$R_1$ and $R_2$ are independently selected from electron donating groups (e.g., alkoxy); and $R_3$ is hydrogen or a $C_1$-$C_{45}$ hydrocarbon radical (e.g., $C_1$-$C_{30}$, $C_1$-$C_{20}$, $C_1$-$C_{10}$, $C_5$-$C_{15}$, $C_5$-$C_{30}$, $C_5$-$C_{40}$, $C_{10}$-$C_{40}$,) optionally substituted with one or more (e.g., 1-20) heteroatoms (e.g., O, S, N, P, F, Cl, Br, I) and wherein $R_3$ may optionally comprise a zwitterionic group (e.g. —Z) and/or a zwitterionic linker group (e.g., —$Z^L$—).

The reaction may proceed through nucleophilic attack by the nitrogen atom in the central ring of the acridan ring system on the carbon atom of $R_L$ to which the triflate leaving group is bonded in the protected sulfonate triflate reactant. In most embodiments, the hydrocarbon linking group (–$R_L$—) of the protected sulfonate triflate comprises a carbon atom bound to the triflate leaving group. An example of such a reaction with a conversion of ≥80% is illustrated by

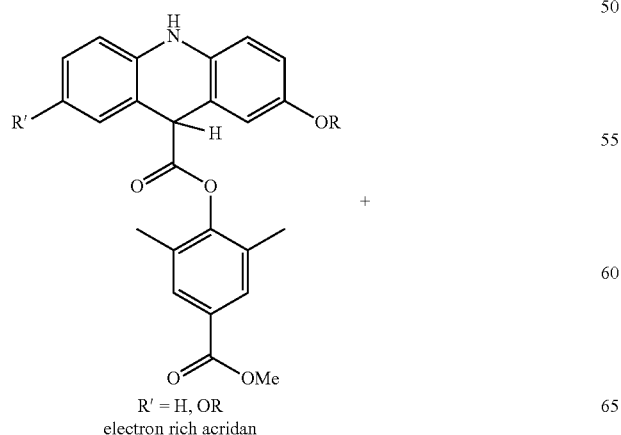

R' = H, OR
electron rich acridan

-continued

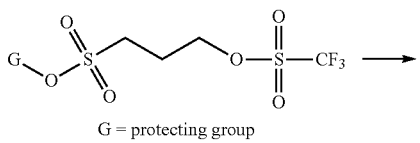

G = protecting group

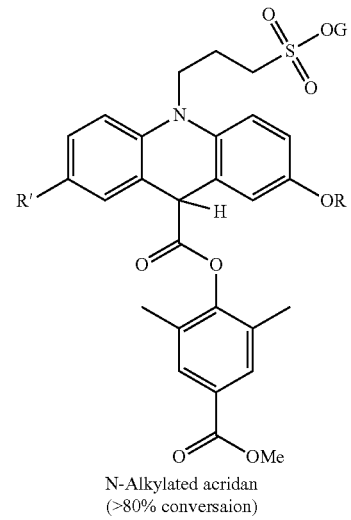

N-Alkylated acridan
(>80% conversaion)

The method for the N-alkylation of an acridan compound may comprise reacting the acridan compound with a protected sulfonate triflate compound having the structure of formula (R1).

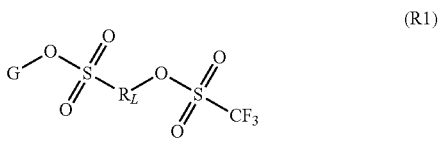

wherein G is an acid-labile protecting group; and —$R_L$— is independently selected at each occurrence from $C_{2-20}$ linear or branched bivalent hydrocarbon radicals; optionally substituted with one or more (e.g., 1-5, one, two, three, four, five) heteroatoms (e.g., O, S, N, P, F, Cl, Br, I), and combinations thereof, and wherein $R_L$ optionally comprises a zwitterionic linker group (e.g., —$Z^L$—). In most embodiments, the acridan is N-alkylated at the central nitrogen of the acridan ring system.

These N-alkylation reactions, while slow, typically proceed in good conversion (≥80%) and the products, N-alkylated acridans, may then be easily oxidized to the N-alkyl acridinium compound (e.g., N-alkyl acridinium esters, N-alkyl acridinium sulfonamides).

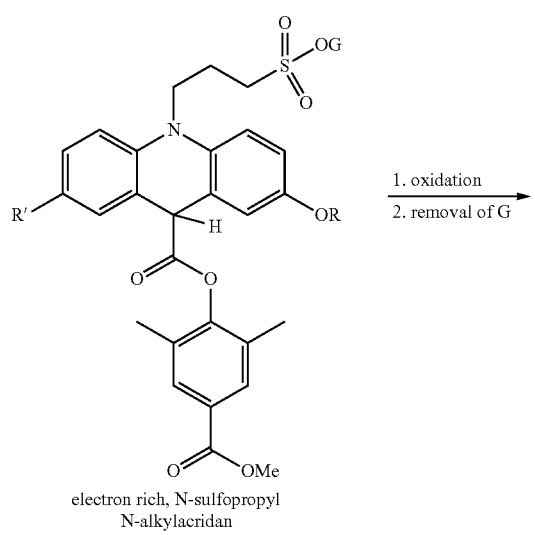

electron rich, N-sulfopropyl
N-alkylacridan 1. oxidation
2. removal of G

electron rich, N-sulfopropyl
acridinium ester

In some embodiments, methods for the synthesis of protected acridinium compounds are also provided comprising:
(a) N-alkylating an acridan with a protected sulfonate triflate; and
(b) oxidizing the N-alkylacridan to convert the N-alkylacridan to a protected acridinium.

The synthesis of N-alkylacridans or N-alkylacridinium may further comprise the reduction of an acridine compound to produce the acridan. In some embodiments, the protected acridinium may be deprotected to produce a zwitterionic acridinium in the presence of acid under conditions compatible with the reactants in such a deprotection.

These N-alkylation reactions using protected sulfonate triflates result in the introduction of a sulfonate with a protecting group attached to a hydrocarbon to the central ring nitrogen of the acridan ring system. Subsequent oxidation of the N-alkylated acridan followed by removal of the protecting group on the sulfonate results in the formation of the alkoxy-substituted N-sulfopropyl acridinium compound. Without wishing to be bound by theory, it is believed that the increased reactivity of the acridans compared to their acridine precursors combined with the increased reactivity of the triflate alkylating reagent is mainly responsible for the increased conversion in this chemical transformation. Moreover, if the acridine analog is used for the N-alkylation reaction rather than the acridan, poor conversions are typically observed. Such poor conversation occurs even with highly reactive triflate alkylating reagents. For example, reaction of 2,7-dimethoxyacridine methyl ester with 3-bromopropyltriflate led to very poor conversion. Similarly, the use of a less reactive alkylating reagent such as a bromide or even iodide with an electron-rich acridan also led to poor conversion.

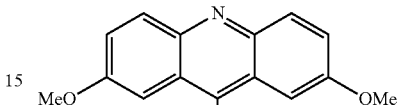

+

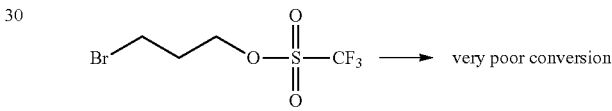

very poor conversion

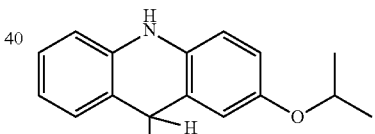

+

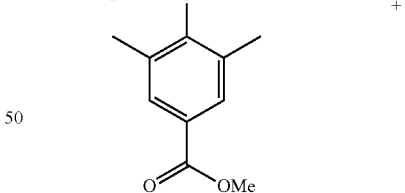

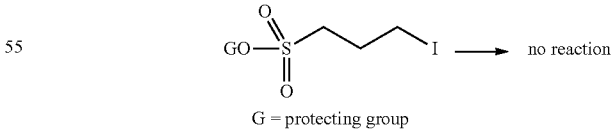

no reaction

G = protecting group

The N-alkylation of reactive, electron-rich acridans with a protected sulfopropyltriflate leads to efficient N-alkylation yielding N-alkylacridans containing sulfonate protecting groups. These N-alkylated acridans may be used in the synthesis of chemiluminescent acridinium compounds. In some embodiments, the N-alkylated acridan may have the structure according to formula (NA1):

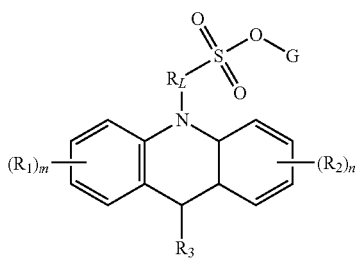

(NA1)

wherein "m" and "n" are independently 0-4 and at least one of "m" or "n" is greater than 0;

$R_1$ and $R_2$ are independently selected from electron donating groups;

$R_3$ is hydrogen or a $C_1$-$C_{45}$ hydrocarbon radical optionally substituted with one or more (e.g., 1-20) heteroatoms (e.g., O, S, N, P, F, Cl, Br, I) and wherein $R_3$ may optionally comprise a zwitterionic group (e.g., —Z) and/or a zwitterionic linker group (e.g., —$Z^L$—);

—$R_L$— is independently selected at each occurrence from $C_{1-20}$ linear or branched bivalent hydrocarbon radicals; optionally substituted with one or more (e.g., 1-5) heteroatoms (e.g., O, S, N, P, F, Cl, Br, I, etc.), and combinations thereof, and wherein $R_L$ optionally comprises a zwitterionic linker group (e.g., —$Z^L$—); and G is an acid-labile protecting group.

The syntheses described herein are particularly useful for N-alkylating electron-rich acridans. For example, the electron-rich acridan may be represented by the structure of formula (A1):

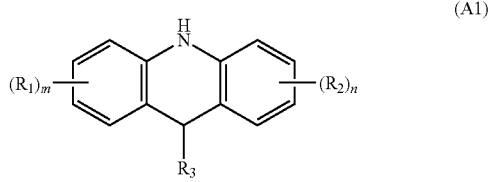

(A1)

wherein "m" and "n" are independently 0-4 and at least one of "m" or "n" is greater than 0;

$R_1$ and $R_2$ are independently selected from electron donating groups; and $R_3$ is hydrogen or a $C_1$-$C_{45}$ hydrocarbon radical (e.g., $C_1$-$C_{30}$, $C_1$-$C_{20}$, $C_1$-$C_{10}$, $C_5$-$C_{15}$, $C_5$-$C_{30}$, $C_5$-$C_{40}$, $C_{10}$-$C_{40}$) optionally substituted with one or more (e.g., 1-20) heteroatoms (e.g., O, S, N, P, F, Cl, Br, I) and wherein $R_3$ may optionally comprise a zwitterionic group (e.g. —Z) and/or a zwitterionic linker group (e.g., —$Z^L$—). These electron-rich acridans are acridan compounds having an electron density greater than the electron density of the same acridan in which $R_1$ and $R_2$ are hydrogen at each occurrence In certain embodiments, acridan is an electron-rich acridan containing alkoxy groups at C-2 and/or C-7 of the acridan ring and, the highly reactive alkylating reagent is a trifluoromethanesulfonate. In preferred embodiments, the alkylating reagent is a sulfonate-protected sulfopropyltriflate leading to an N-alkylated acridan containing an N-sulfopropyl group with a protecting group on the sulfonate. Oxidation of the acridan to the acridinium ester followed by removal of the protecting group on the sulfonate leads to a protected acridinium compound. The protected acridinium compound may have the structure

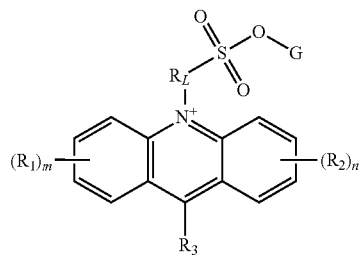

This synthetic protocol completely eliminates the use of the carcinogenic chemical 1,3-propane sultone for the assembly of high light yield, electron-rich acridinium esters. The elimination of the carcinogenic alkylating reagent 1,3-propane sultone provides a more environmentally-friendly synthesis of these high light output labels for clinical diagnostics. Moreover, such reaction may or may not occur in the presence of ionic liquids. The chemical synthesis described herein utilize the reactivity of the acridan separate from the functional group at the C-9 position of the acridinium ring (i.e., the carbon bound to $R_3$ in formula (A1)). Typically, this functional group provides chemiluminescence in acridinium complexes by formations of excited state acridone, which is the light emitting species. Since the functional group at C-9 is not implicated in these N-alkylation schema, the synthetic mechanisms described herein operate with a variety of acridan compounds including acridan esters and acridan sulfonamides. In some embodiments, the acridan is an acridan ester. In other embodiments, the acridan is an acridan sulfonamide. Accordingly, various classes of chemiluminescent acridinium compounds (and their respective intermediates) may be produced by the methods described, including chemiluminescent acridinium esters and chemiluminescent acridinium sulfonamides.

DETAILED DESCRIPTION

Figure 1:
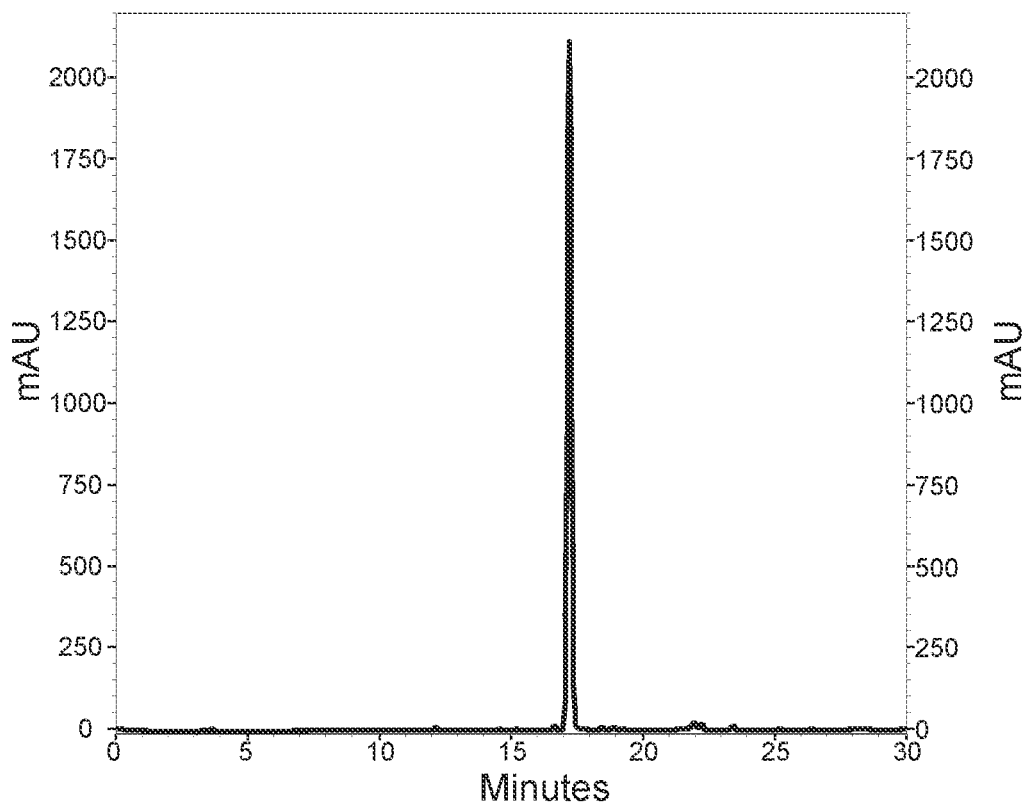
FIG. 1 is an HPLC trace of N-sulfopropyl isopropoxy acridinium ester (Compound 5) synthesized using the methods of the current invention.

For convenience, certain terms employed in the specification, including the examples and appended claims, are collected here. Unless defined otherwise, all technical and scientific terms used herein have the same meaning as commonly understood by one of ordinary skill in the art to which this disclosure pertains.

Unless otherwise explicitly defined, the following terms and phrases are intended to have the following meanings throughout this disclosure:

All percentages given herein refer to the weight percentages of a particular component relative to the entire composition, including the carrier, unless otherwise indicated. It will be understood that the sum of all weight % of individual components within a composition will not exceed 100%.

The terms "a" or "an," as used in herein means one or more. As used herein, the term "consisting essentially of" is intended to limit the invention to the specified materials or steps and those that do not materially affect the basic and novel characteristics of the claimed invention, as understood from a reading of this specification.

The following definitions of various groups or substituents are used, unless otherwise described. Specific and general values listed below for radicals, substituents, and ranges, are for illustration only; they do not exclude other defined values or other values within defined ranges for the radicals and substituents. Unless otherwise indicated, alkyl, alkenyl, alkynyl, alkoxy, and the like denote straight, branched, and cyclic groups, as well as any combination thereof.

The term "hydrocarbon" refers to a radical or group containing carbon and hydrogen atoms. Examples of hydrocarbon radicals include, without limitation, alkyl, alkenyl, alkynyl, aryl, aryl-alkyl, alkyl-aryl, and any combination thereof (e.g., alkyl-aryl-alkyl, etc.). As used herein, unless otherwise indicated, hydrocarbons may be monovalent or multivalent (e.g., divalent, trivalent, etc) hydrocarbon radicals. A radical of the form $—(CH_2)_n—$, including a methylene radical, i.e., $—CH_2—$, is regarded as an alkyl radical if it does not have unsaturated bonds between carbon atoms. Unless otherwise specified, all hydrocarbon radicals (including substituted and unsubstituted alkyl, alkenyl, alkynyl, aryl, aryl-alkyl, alkyl-aryl, etc.) may have from 1-45 carbon atoms (e.g., $C_1$-$C_{30}$, $C_1$-$C_{20}$, $C_1$-$C_{10}$, $C_5$-$C_{15}$, $C_5$-$C_{30}$, $C_5$-$C_{40}$, $C_{10}$-$C_{40}$, $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$). In certain embodiments, hydrocarbons will have from 5-35 or from 1-20 or from 1-12 or from 1-8 or from 1-6 or from 1-3 carbon atoms, including for example, embodiments having one, two, three, four, five, six, seven, eight, nine, or ten carbon atoms. For example, hydrocarbons may have from about 2 to about 70 atoms or from 4 to about 60 atoms or from 4 to about 20 atoms.

A "substituted" hydrocarbon may have as a substituent one or more hydrocarbon radicals, substituted hydrocarbon radicals, or may comprise one or more heteroatoms. Any hydrocarbon substituents disclosed herein may optionally include from 1-20 (e.g., 1-10, 1-5, etc.) heteroatoms. Examples of substituted hydrocarbon radicals include, without limitation, heterocycles, such as heteroaryls. Unless otherwise specified, a hydrocarbon substituted with one or more heteroatoms will comprise from 1-20 heteroatoms. In other embodiments, a hydrocarbon substituted with one or more heteroatoms will comprise from 1-12 or from 1-8 or from 1-6 or from 1-4 or from 1-3 or from 1-2 heteroatoms. Examples of heteroatoms include, but are not limited to, oxygen, nitrogen, sulfur, phosphorous, halogen (e.g., F, Cl, Br, I), boron, silicon, etc. In some embodiments, heteroatoms will be selected from the group consisting of oxygen, nitrogen, sulfur, phosphorous, and halogen (e.g., F, Cl, Br, I). In preferred embodiments, the heteroatoms may be selected from O, N, or S. In some embodiments, a heteroatom or group may substitute a carbon. In some embodiments, a heteroatom or group may substitute hydrogen. In some embodiments, a substituted hydrocarbon may comprise one or more heteroatoms in the backbone or chain of the molecule (e.g., interposed between two carbon atoms, as in "oxa"). In some embodiments, a substituted hydrocarbon may comprise one or more heteroatoms pendant from the backbone or chain of the molecule (e.g., covalently bound to a carbon atom in the chain or backbone, as in "oxo").

In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

In some embodiments, any hydrocarbon or substituted hydrocarbon disclosed herein may be substituted with one or more (e.g., from 1-6 or from 1-4 or from 1-3 or one or two or three) substituents $X^{sub}$, where $X^{sub}$ is independently selected at each occurrence from one or more (e.g., 1-20) heteroatoms or one or more (e.g., 1-10) heteroatom-containing groups, or $X^{sub}$ is independently selected at each occurrence from $—F$, $—Cl$, $—Br$, $—I$, $—OH$, $—OR^*$, $—NH_2$, $—NHR^*$, $—N(R^*)_2$, $—N(R^*)_3^+$, $—N(R^*)—OH$, $—N(→O)(R^*)_2$, $—O—N(R^*)_2$, $—N(R^*)—O—R^*$, $—N(R^*)=N(R^*)_2$, $—C=N—R^*$, $—N=C(R^*)_2$, $—C=N—N(R^*)_2$, $—C(=NR^*)(—N(R^*)_2)$, $—C(H)(=N—OH)$, $—SH$, $—SR^*$, $—CN$, $—NC$, $—CHF_2$, $—CCl_3$, $—CF_2Cl$, $—CFCl_2$, $—C(=O)—R^*$, $—CHO$, $—CO_2H$, $—C(O)CH_3$, $—CO_2$, $—CO_2R^*$, $—C(=O)—S—R^*$, $—O—(C=O)—H$, $—O—(C=O)—R^*$, $—S—C(=O)—R^*$, $—(C=O)—NH_2$, $—C(=O)—N(R^*)_2$, $—C(=O)—NHNH_2$, $—O—C(=O)—NHNH_2$, $—C(=S)—NH_2$, $—(C=S)—N(R^*)_2$, $—N(R^*)—CHO$, $—N(R^*)—C(=O)—R^*$, $—C(=NR)—OR^*$, $—O—C(=NR^*)—R^*$, $—SCN$, $—NCS$, $—NSO$, $—SSR^*$, $—N(R^*)—C(=O)—N(R^*)_2$, $—CH_3$, $—CH_2—CH_3$, $—CH_2—CH_2—CH_3$, $—C(H)(CH_2)_2$, $—C(CH_3)_3$, $—N(R^*)—C(=S)—N(R^*)_2$, $—S(=O)_{1-2}—R^*$, $—O—S(=O)_2—R^*$, $—S(=O)_2—OR^*$, $—N(R^*)—S(=O)_2—R^*$, $—S(=O)_2—N(R^*)_2$, $—O—SO_3$, $—O—S(=O)_2—OR^*$, $—O—S(=O)—OR^*$, $—O—S(=O)—R^*$, $—S(=O)—OR^*$, $—S(=O)—R^*$, $—NO$, $—NO_2$, $—NO_3$, $—O—NO$, $—O—NO_2$, $—N_3$, $—N_2—R^*$, $—N(C_2H_4)$, $—Si(R^*)_3$, $—CF_3$, $—O—CF_3$, $—O—CHF_2$, $—O—CH_3$, $—O—(CH_2)_{1-6}CH_3$, $—OC(H)(CH_2)_2$, $—OC(CH_3)_3$, $—PR^*_2$, $—O—P(=O)(OR^*)_2$, or $—P(=O)(OR^*)_2$; where, independently at each occurrence, $R^*$ may be H or a $C_{1-10}$ or $C_{1-8}$ or $C_{1-6}$ or $C_{1-4}$ unsubstituted hydrocarbon, including without limitation alkyl, alkenyl, alkynyl, aryl (e.g., phenyl), alkyl-aryl (e.g., benzyl), aryl-alkyl (e.g., toluyl). In some embodiments, $X^{sub}$ may comprise a $C_1$-$C_8$ or $C_1$-$C_6$ or $C_2$-$C_4$ perfluoroalkyl. In some embodiments, X may be a $C_1$-$C_8$ or $C_2$-$C_6$ or $C_3$-$C_5$ heterocycle (e.g., heteroaryl radical). The term "halo" or "halogen" refers to any radical of fluorine, chlorine, bromine or iodine. In certain embodiments, $X^{sub}$ is independently selected at each occurrence from $—OH$, $—SH$, $—NH_2$, $—N(R^*)_2$, $—C(O)OR^*$, $—C(O)NR^*R^*$, $—C(O)NR^*R^*$, $—C(O)OH$, $—C(O)NH_2$, F, or $—Cl$. In some embodiments, $X^{sub}$ is F. In some embodiments, $R^*$ is hydrogen, or lower alkyl (e.g., $C_1$-$C_5$ linear or branched alkyl such as methyl, ethyl, propyl, or isopropyl). In some embodiments, $R^*$ is hydrogen, or lower alkoxy (e.g., $C_1$-$C_5$ linear or branched alkoxy such as methoxy, ethoxy, propoxy, or isopropoxy). In some embodiments, $X^{sub}$ is $—CF_3$ or $—O—CF_3$. In some embodiments, $X^{sub}$ may provide an anionic charge to counterbalance any cationic charge directly or indirectly covalently attached and in order to form a zwitterion (e.g., in zwitterionic linking groups-$Z^L$- or zwitterionic groups-Z). In some embodiments, $X^{sub}$ may be carboxylate (—C(O)O⁻), sulfonate (—SO₃⁻), sulfate (—OSO₃⁻), phosphate (—OP(O)(OR^P)O⁻), or oxide (—O—), and $R^P$ is hydrogen or $C_{1-12}$ hydrocarbon optionally substituted with up to 10 heteroatoms.

It will be understood that the description of compounds herein is limited by principles of chemical bonding known to those skilled in the art. Accordingly, where a group may be substituted by one or more of a number of substituents, such substitutions are selected so as to comply with principles of chemical bonding with regard to valencies, etc., and to give compounds which are not inherently unstable. For example, any carbon atom will be bonded to two, three, or four other atoms, consistent with the four valence electrons of carbon.

In general, and unless otherwise indicated, substituent (radical) prefix names are derived from the parent hydride by either (i) replacing the "ane" or in the parent hydride with the suffixes "yl," "diyl," "triyl," "tetrayl," etc.; or (ii) replacing the "e" in the parent hydride with the suffixes "yl," "diyl," "triyl," "tetrayl," etc. (here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Radicals of steroids may also be designated with the "yl," "diyl," "triyl," "tetrayl," etc. suffixes. Conventional numbering/lettering systems are also adhered to for substituent numbering and the nomenclature of fused, spiro, bicyclic, tricyclic, polycyclic rings.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substituents. Examples of alkyl groups include without limitation methyl, ethyl, n-propyl, isopropyl, and tert-butyl. Any alkyl group referenced herein (e.g., R, R', R", $R_1$, $R_2$, $R_3$, $R_4$, $R_5$) may have from 1-45 carbon atoms. In other embodiments, alkyl groups will have from 1-30 or from 1-20 or from 1-12 or from 1-8 or from 1-6 or from 1-3 carbon atoms, including for example, embodiments having one, two, three, four, five, six, seven, eight, nine, or ten carbon atoms.

The term "haloalkyl" refers to an alkyl group, in which at least one hydrogen atom is replaced by halo. In some embodiments, more than one hydrogen atom (e.g., 2, 3, 4, 5, 6, 7, 8, 9, 10, 11, 12, 13, or 14, etc.) are replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—OCH₃), ethoxy, propoxy, isopropoxy, butoxy, iso-butoxy, sec-butoxy, pentoxy, 2-pentoxy, 3-pentoxy, or hexyloxy. Likewise, the term "thioalkoxy" refers to a group of formula —S(alkyl). Finally, the terms "haloalkoxy" and "halothioalkoxy" refer to —O(haloalkyl) and —S(haloalkyl), respectively. As used herein, the term "hydroxyl," employed alone or in combination with other terms, refers to a group of formula-OH. Hydroxyalkyl refers to an alkyl group substituted with hydroxy (e.g., -(alkyl)-OH). Any alkoxy, thioalkoxy, or haloalkoxy group referenced herein (e.g., R, R', R", $R_1$, $R_2$, $R_3$, $R_4$, $R_5$, $R_6$, $R_7$, $R_8$, $R_9$, $R_{10}$, $R_{11}$, $R_{12}$) may have from 1-35 carbon atoms. In other embodiments, alkyl, alkoxy, thioalkoxy, or haloalkoxy groups will have from 1-30 or from 1-20 or from 1-12 or from 1-8 or from 1-6 or from 1-3 carbon atoms, including for example, embodiments having one, two, three, four, five, six, seven, eight, nine, or ten carbon atoms.

The term "aralkyl" refers to an alkyl moiety in which an alkyl hydrogen atom is replaced by an aryl group (e.g., phenyl, naphthyl). One of the carbons of the alkyl moiety serves as the point of attachment of the aralkyl group to another moiety. Any ring or chain atom can be optionally substituted, e.g., by one or more substituents. Non-limiting examples of "aralkyl" include benzyl, 2-phenylethyl, and 3-phenylpropyl groups.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent. Any alkenyl group referenced herein (e.g., R, R', R", $R_1$, $R_2$, $R_3$, $R_4$, $R_5$, $R_6$, $R_7$, $R_8$, $R_9$, $R_{10}$, $R_{11}$, $R_{12}$) may have from 1-35 carbon atoms. In other embodiments, alkenyl groups will have from 1-20 or from 1-12 or from 1-8 or from 1-6 or from 1-3 carbon atoms, including for example, embodiments having one, two, three, four, five, six, seven, eight, nine, or ten carbon atoms.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include, e.g., ethynyl, propargyl, and 3-hexynyl. One of the triple bond carbons can optionally be the point of attachment of the alkynyl substituent.

The term "heterocyclyl" refers to a fully saturated, partially saturated, or aromatic monocyclic, bicyclic, tricyclic, or other polycyclic ring system having one or more constituent heteroatom ring atoms independently selected from O, N (it is understood that one or two additional groups (e.g., $R^N$) may be present to complete the tertiary nitrogen valence and/or form a salt unless otherwise indicated), or S. The heteroatom or ring carbon can be the point of attachment of the heterocyclyl substituent to another moiety. Any atom can be optionally substituted, e.g., with one or more substituents (e.g. heteroatoms or groups $X^{sub}$). Heterocyclyl groups can include, e.g., tetrahydrofuryl, tetrahydropyranyl, piperidyl (piperidino), piperazinyl, morpholinyl (morpholino), pyrrolinyl, and pyrrolidinyl. By way of example, the phrase "heterocyclic ring containing from 5-6 ring atoms, wherein from 1-2 of the ring atoms is independently selected from N, NH, N($C_1$-$C_6$ alkyl), NC(O)($C_1$-$C_6$ alkyl), O, and S; and wherein said heterocyclic ring is optionally substituted with from 1-3 independently selected R" would include (but not be limited to) tetrahydrofuryl, tetrahydropyranyl, piperidyl (piperidino), piperazinyl, morpholinyl (morpholino), pyrrolinyl, and pyrrolidinyl.

The term "heterocycloalkenyl" refers to partially unsaturated monocyclic, bicyclic, tricyclic, or other polycyclic hydrocarbon groups having one or more (e.g., 1-4) heteroatom ring atoms independently selected from O, N (it is understood that one or two additional groups may be present to complete the nitrogen valence and/or form a salt), or S. A ring carbon (e.g., saturated or unsaturated) or heteroatom can be the point of attachment of the heterocycloalkenyl substituent. Any atom can be optionally substituted, e.g., by one or more substituents. Heterocycloalkenyl groups can include, e.g., dihydropyridyl, tetrahydropyridyl, dihydropyranyl, 4,5-dihydrooxazolyl, 4,5-dihydro-1H-imidazolyl, 1,2,5,6-tetrahydro-pyrimidinyl, and 5,6-dihydro-2H-[1,3]oxazinyl.

The term "cycloalkyl" refers to a fully saturated monocyclic, bicyclic, tricyclic, or other polycyclic hydrocarbon groups. Any atom can be optionally substituted, e.g., by one or more substituents. A ring carbon serves as the point of attachment of a cycloalkyl group to another moiety. Cycloalkyl moieties can include, e.g., cyclopropyl, cyclobutyl, cyclopentyl, cyclohexyl, cycloheptyl, adamantyl, and norbornyl (bicycle[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted, e.g., by one or more substituents. Cycloalkenyl moieties can include, e.g., cyclohexenyl, cyclohexadienyl, or norbornenyl.

As used herein, the term "cycloalkylene" refers to a divalent monocyclic cycloalkyl group having the indicated number of ring atoms.

As used herein, the term "heterocycloalkylene" refers to a divalent monocyclic heterocyclyl group having the indicated number of ring atoms.

The term "aryl" refers to an aromatic monocyclic, bicyclic (2 fused rings), or tricyclic (3 fused rings), or polycyclic (>3 fused rings) hydrocarbon ring system. One or more ring atoms can be optionally substituted, e.g., by one or more substituents. Aryl moieties include, e.g., phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S in the ring. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

In general, when a definition for a particular variable includes both hydrogen and non-hydrogen (e.g., halo, alkyl, aryl) possibilities, the term "substituent(s) other than hydrogen" refers collectively to the non-hydrogen possibilities for that particular variable.

In general, the limits (end points) of any range recited herein are within the scope of the invention and should be understood to be disclosed embodiments. For example, a range of 0 to 4 expressly discloses 0, 1, 2, 3, 4, and any subset within that range (e.g., from 0 to 2, from 0 to 3, from 0 to 4, from 1 to 2, from 1 to 3, from 1 to 4, from 2 to 3, from 2 to 4, from 3 to 4).

The term "substituent" refers to a group "substituted" on, e.g., an alkyl, haloalkyl, cycloalkyl, heterocyclyl, heterocycloalkenyl, cycloalkenyl, aryl, or heteroaryl group at any atom of that group, replacing one or more hydrogen atoms therein. In one aspect, the substituent(s) on a group are independently any one single, or any combination of two or more of the permissible atoms or groups of atoms delineated for that substituent. In another aspect, a substituent may itself be substituted with any one of the above substituents. Further, as used herein, the phrase "optionally substituted" means unsubstituted (e.g., substituted with an H) or substituted. It is understood that substitution at a given atom is limited by valency. Common substituents include halo (e.g. F), $C_{1-12}$ straight chain or branched chain alkyl, $C_{2-12}$ alkenyl, $C_{2-12}$ alkynyl, $C_{3-12}$ cycloalkyl, $C_{6-12}$ aryl, $C_{3-12}$ heteroaryl, $C_{3-12}$ heterocyclyl, $C_{1-12}$ alkylsulfonyl, nitro, cyano, —COOR, —C(O)NRR', —OR, —SR, —NRR', and oxo, such as mono- or di- or tri-substitutions with moieties such as trifluoromethoxy, chlorine, bromine, fluorine, methyl, methoxy, pyridyl, furyl, triazyl, piperazinyl, pyrazoyl, imidazoyl, and the like, each optionally containing one or more heteroatoms such as halo, N, O, S, and P. R and R' are independently hydrogen, $C_{1-12}$ alkyl, $C_{1-12}$ haloalkyl, $C_{2-12}$ alkenyl, $C_{2-12}$ alkynyl, $C_{3-12}$ cycloalkyl, $C_{4-24}$ cycloalkylalkyl, $C_{6-12}$ aryl, $C_{7-24}$ aralkyl, $C_{3-12}$ heterocyclyl, $C_{3-24}$ heterocyclylalkyl, $C_{3-12}$ heteroaryl, or $C_{4-24}$ heteroarylalkyl. Unless otherwise noted, all groups described herein optionally contain one or more common substituents, to the extent permitted by valency. As used herein, the term "substituted" means that a hydrogen and/or carbon atom is removed and replaced by a substituent (e.g., a common substituent). The use of a substituent (radical) prefix names such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo. Similarly, the use of "heteroalkyl" and other "hetero" modified hydrocarbons without the modifier "optionally substituted" is still understood to mean that a carbon atom in the hydrocarbon is replaced by O, N, or S.

In some embodiments the hydrocarbon (e.g., R, R', R", $R_1$, $R_2$, $R_3$, $R_4$, $R_5$, $R_6$, $R_7$, $R_8$, $R_9$, $R_{10}$, $R_{11}$, $R_{12}$) comprises a groups -L or —$R_L$-L, where L is a derivitizable functional group comprising a leaving group, electrophilic group, or nucleophilic group for forming a conjugate with an analyte, analyte analog, or binding partner for an analyte. In some embodiments, L will be selected from the group consisting of:

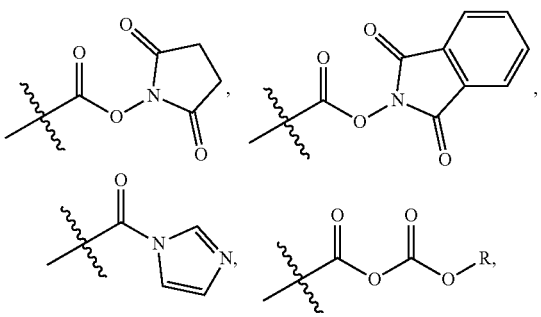

-continued

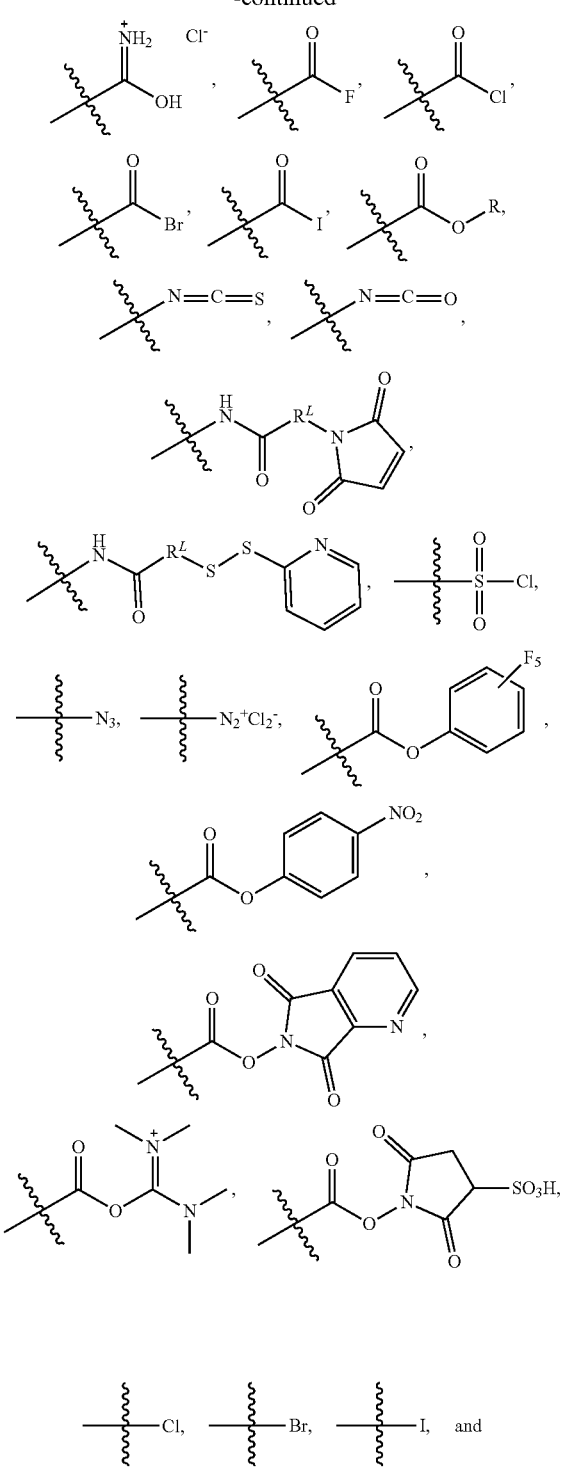

wherein R is independently at each occurrence hydrogen or a $C_1$-$C_{10}$ hydrocarbon (e.g., alkyl, alkenyl, alkynyl, aryl, arylalkyl); and $R_L$ is a bivalent $C_1$-$C_{10}$ hydrocarbon (e.g., alkyl, alkenyl, alkynyl, aryl, arylalkyl).

In some embodiments, the hydrocarbon may comprise a zwitterionic group. The zwitterionic group may have the form:

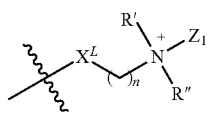

wherein $X^L$ is independently selected at each occurrence from a bond, —$CH_2$—, oxygen, sulfur, —$NR^N$—, amide (~$NR^N(CO)$—), carbamate (—$NR^NC(O)O$—), or urea (—$NR^NC(O)NR^N$—);

R' and R" are independently selected at each occurrence from $C_{1-35}$ alkyl, alkenyl, alkynyl, aryl, or aralkyl, each containing up to 20 heteroatoms;

$Z_1$ is a group —$R_L$—$X^a$ where $X^a$ is an anionic group such as carboxylate (—$COO^-$), sulfonate (~$SO_3^-$), sulfate (~$OSO_3^-$), phosphate (—$OP(O)(OR^P)(O^-)$), or oxide (—O n is, independently selected at each occurrence, an integer between one and 12;

$R^P$ is independently selected at each occurrence from $C_{1-35}$ alkyl, alkenyl, alkynyl, aryl, or aralkyl groups each containing up to 20 heteroatoms;

$R_L$ may be absent (i.e., it is a bond) or a divalent radical selected from $C_{1-35}$ alkyl, alkenyl, alkynyl, aryl, or aralkyl group, each optionally containing up to 20 heteroatoms; and $R^N$ is lower alkyl (e.g., $C_1$-$C_4$ linear or branched alkyl such as methyl, ethyl, propyl, isopropyl, butyl, isobutyl). More particularly, Z may be a group:

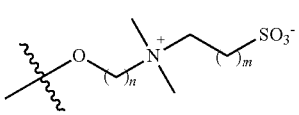

where n is an integer from 1-12 and m is an integer from 0-3.

In some embodiments, a hydrocarbon may (e.g., —$R_L$—, R, R', R", $R_1$, $R_2$, $R_3$, $R_4$, $R_5$, $R^6$, $R_7$, $R_8$, $R_9$, $R_{10}$, $R_{11}$, $R_{12}$) comprise may comprise a zwitterionic linker or a bivalent hydrocarbon linker with a zwitterionic linking moiety. The zwitterionic linker may have the structure:

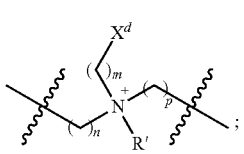

wherein "m" is 0 (i.e. it is a bond) or 1;
"n" and "p" are independently at each occurrence an integer from 0 (i.e. it is a bond) to 10;
$X^a$ is an anionic group; and
R' is hydrogen or lower alkyl (e.g., is methyl, ethyl, propyl, isopropyl, butyl, isobutyl, pentyl, etc.). Preferred zwitterionic linkers have the formula:

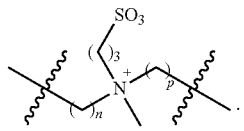

The present invention provides compounds and methods for the synthesis of chemiluminescent acridinium compounds. Such compounds are able to be prepared without the carcinogenic reagent 1,3-propane sultone in the synthesis of these commercially useful, high light yield, electron-rich chemiluminescent acridinium labels containing N-sulfopropyl groups (e.g., acridinium dimethylphenyl esters, acridinium esters, acridinium sulfonamides). Moreover, these synthetic protocols provide for the synthesis of a variety of acridinium compounds with different functional groups attached to the central nitrogen of the acridinium ring system.

Exemplary high light yield, electron-rich acridinium esters capable of forming a conjugate with an analyte, analyte analog or other binding partner include acridinium esters 1, 2, 3, and 4. For acridinium esters 1 and 2 that contain a C-2 isopropoxy group, compound 5 is the common advanced synthetic intermediate used for final assembly of these acridinium esters. For the dialkoxy compounds 3 and 4, compounds 6 and 7 represent the advanced synthetic intermediates respectively. The present invention includes compounds and methods useful for the production of compounds 5, 6, and 7 which are important precursors to Compounds 1-4. Compound 1-4 all display increased light output of 2-3 fold compared to unsubstituted acridinium esters (i.e., compounds without substitution at the and C(2) and C(7) positions) and are useful labels for improving sensitivity of immunoassays. Moreover, these production methods occur without the use of carcinogens like 1,3-propane sultone. Additionally, use of the reagents and protocols described herein allows for the attachment of sulfopropyl groups to the two ether oxygens of compound 7 without the use of 1,3-propane sultone.

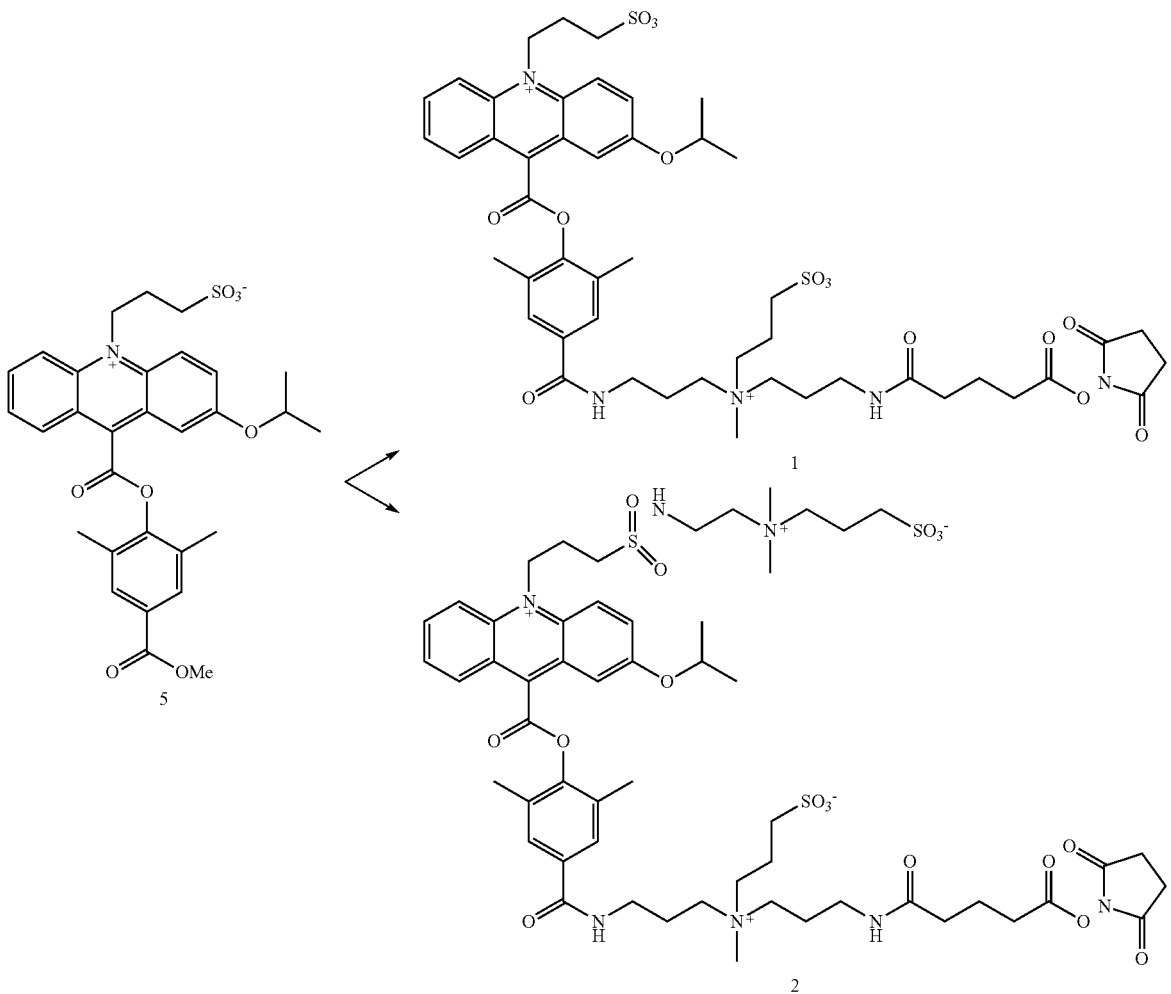

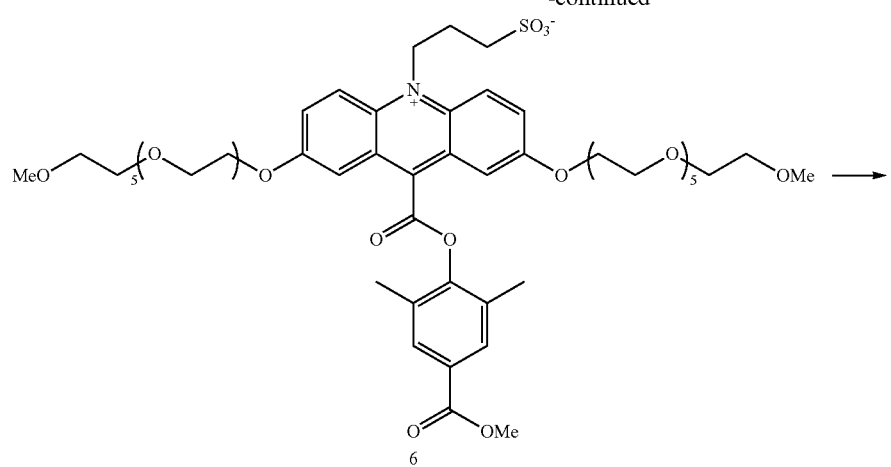
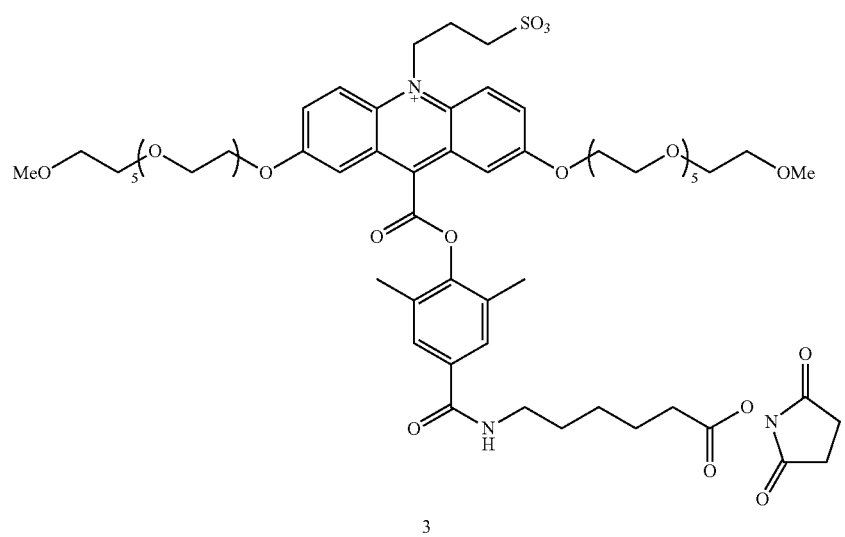
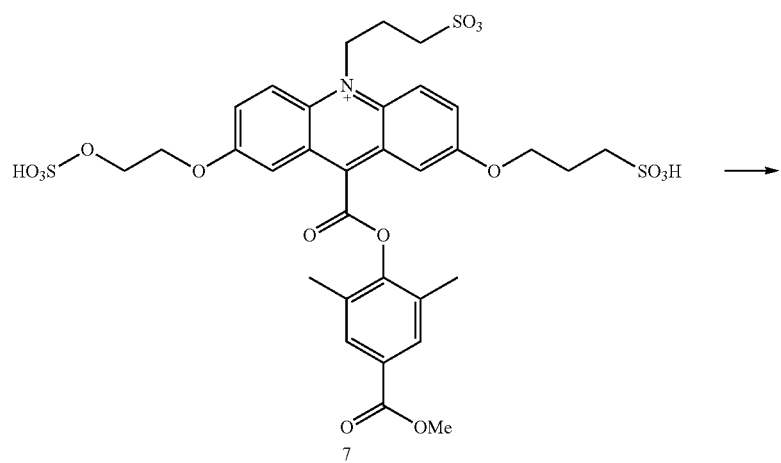

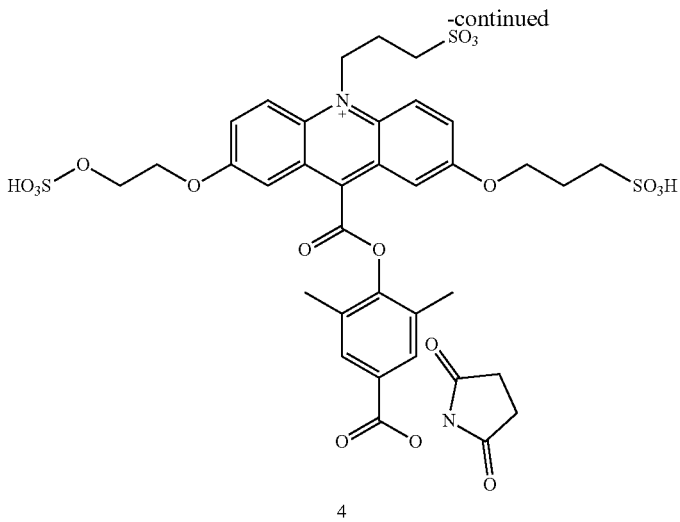

4

The acridans may be N-alkylated by reacting the acridan with a protected sulfonate triflate compound having the structure of formula (R1):

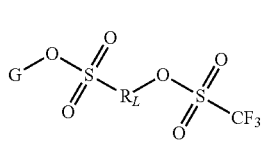

(R1)

wherein G is an acid-labile protecting group; and
—$R_L$— is independently selected at each occurrence from $C_{1-20}$ linear or branched bivalent hydrocarbon radicals; optionally substituted with one or more (e.g., 1-5, one, two, three, four, five) heteroatoms (e.g., O, S, N, P, F, Cl, Br, I), and combinations thereof, and wherein $R_L$ optionally comprises a zwitterionic linker group (e.g., —$Z^L$—). In some embodiments, the $R^L$ of said sulfonate triflate compound is lower alkyl (e.g., $C_1$-$C_4$ linear or branched alkyl such as methyl, ethyl, propyl, butyl). In some embodiments, the sulfonate triflate compound has the structure of formula (R2):

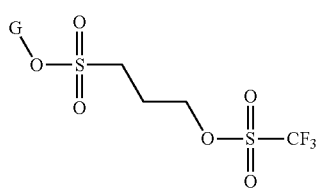

(R2)

Typically, the protecting group for the sulfonate in the sulfonate triflate undergoes cleavage from the sulfonate in acidic conditions. Such protecting groups have been described in Adamczyk et al, *J. Org. Chem.* 63 (1998): 5636-5639; Miller, *J. Org. Chem.* 75 (2010): 4632-4635; and Pauff and Miller, *J. Org. Chem.* 78 (2013): 711-716) each hereby incorporated by reference by their entirety and specifically in relation to sulfonate protecting groups and cleavage reactions. In some embodiments, G is selected from

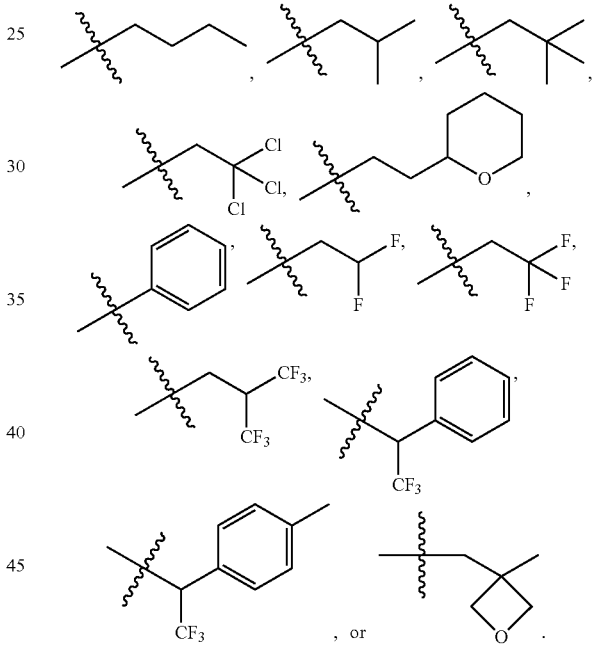

In more preferred, embodiments, G is selected from

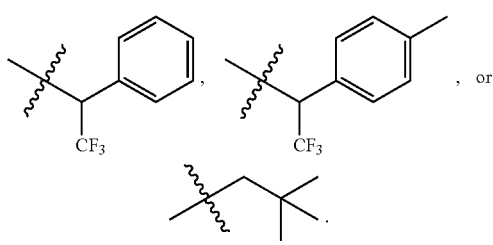

Typically, neopentyl protecting groups require strong acid for their removal. Additionally, synthesis of these groups requires using toxic oxirane and an organometallic reagent butyl lithium. (Adamczyk et al.). The α-trifluoromethylbenzyl (TFMB) sulfonates, TFMB and its 4'-methyl version (4'-Me-TFMB) are stable to mild acid and were described by Miller et al based on solvolysis studies of analogous compounds as reported by Allen et al, *J. Am. Chem. Soc.* 105 (1983): 2343-2354, each hereby incorporated by reference by their entirety and specifically in relation to sulfonate protecting groups and cleavage reactions. The protecting group may be cleaved following N-alkylation of the acridan. Preferably, the protecting group is cleaved from an acridinium compound formed from the oxidation of the N-alkylated acridans.

Persons of ordinary skill are able to synthesize these protected sulfonate triflates. For example, iodopropylsulfonate 4'-methyl TFMB ester may be converted to the more reactive triflate by stirring the iodide with silver trifluoromethanesulfanate in tolune. In some embodiments, the invention provides the synthesis of protected sulfonate triflates comprising reacting a compound having the structure:

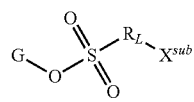

with silver trifluoromethane sulfonate to produce a protected sulfonate triflate having the structure of formula (R1):

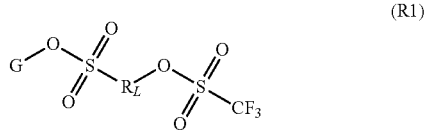

wherein $R_L$ is a bivalent hydrocarbon (e.g., propyl), and $X^{sub}$ is halogen (e.g., —I). In certain embodiments G is:

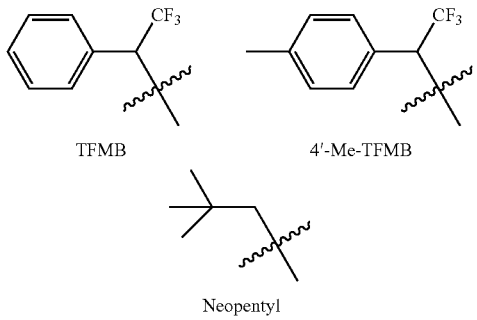

Preferred alkylating reagents for the introduction of the N-sulfopropyl group can be represented by the formula:

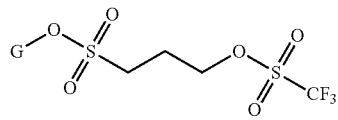

In most embodiments, G is selected from the following:

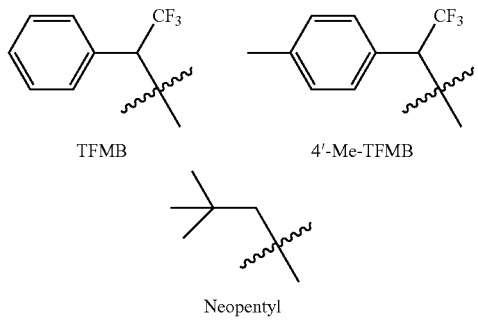

In preferred embodiments, G is 4'-Me-TFMB.

Typically, the cleavage reaction of the protected sulfonate protecting group occurs in an acid compatible with the acridan, acridine, or acridinium reactants. In some embodiments, the acid is a Brönsted acid which may be selected from hydrochloric acid, hydrobromic acid, sulphuric acid, benzenesulphonic acid, p-toluenesulphonic acid (p-TSA), methanesulphonic acid, ethanesulphonic acid, trifluoromethanesulfonic acid (TFMSA), trifluoroacetic acid (TFA), trichloroacetic acid (TCA), dichloroacetic acid (DCA), chloroacetic acid, formic acid and acetic acid. In some embodiments, the acid may be a Lewis acid or a silicon compound or a combination of two or more such acids and/or silicon compounds. The acid may be selected from boron trifluoride, boron trichloride, boron tribromide, aluminium chloride, tin chloride, titanium chloride, silicon tetrachloride, chlorotrimethylsilane $Me_3SiCl$ (TMSCl), bromotrimethylsilane $Me_3SiBr$ (TMSBr) and trimethylsilyl trifluoromethanesulphonate (TMSOTf). In preferred embodiments, the acid for cleavage of the sulfonate protecting group may be trifluoroacetic acid (TFA), hydrochloric acid, or sulfuric acid etc.

The invention provides methods of N-alkylating acridans, and specifically, electron-rich acridans. Accordingly, these methods allow for the introduction of a hydrophilic, N-sulfopropyl group into a high light yield, electron-rich chemiluminescent acridinium ester containing one or more alkoxy groups in the acridinium ring by (a) conversion of the acridine ester precursor to the corresponding acridan using a reducing reagent; (b) N-alkylation of the acridan ester with a sulfopropyl triflate where the sulfonate contains an acid-labile protecting group by stirring the two components in a solvent under an inert atmosphere; (c) oxidation of the N-sulfopropylacridan with the protected sulfonate to the N-sulfopropyl acridinium ester and; (d) cleavage of the sulfonate protecting group by acid hydrolysis. The acridan may have the structure according to formula (A1):

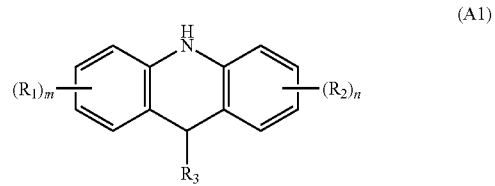

wherein "m" and "n" are independently 0-4 and at least one of "m" or "n" is greater than 0;

$R_1$ and $R_2$ are independently selected from electron donating groups; and $R_3$ is hydrogen or a $C_1$-$C_{45}$ hydrocarbon radical (e.g., $C_1$-$C_{30}$, $C_1$-$C_{20}$, $C_1$-$C_{10}$, $C_5$-$C_{15}$, $C_5$-$C_{30}$, $C_5$-$C_{40}$, $C_{10}$-$C_{40}$) optionally substituted with one or more (e.g., 1-20) heteroatoms (e.g., O, S, N, P, F, Cl, Br, I) and wherein $R_3$ may optionally comprise a zwitterionic group (e.g. —Z) and/or a zwitterionic linker group (e.g., —$Z^L$—). In some embodiments, $R_1$ and/or $R_2$ are alkoxy. In some embodiments, $R_1$ and $R_2$ are each the same alkoxy group (e.g. lower alkoxy such as methoxy, ethoxy, propoxy, isopropoxy, etc). In other embodiments, wherein $R_1$ or $R_2$ is hydrogen and the other of $R_1$ or $R_2$ is alkoxy (e.g. lower alkoxy such as methyl, ethoxy, isopropoxy, isopropoxy, etc.). R1 and/or R2 may be independently selected from alkoxy groups having the structure:

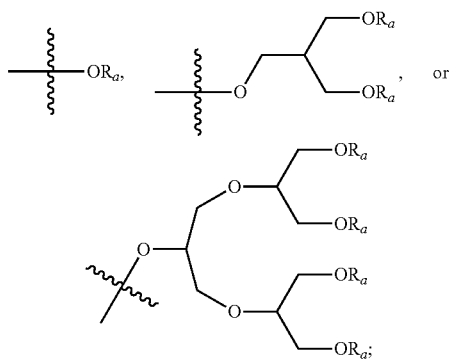

wherein $R_a$ is independently selected at each occurrence from methyl, isopropyl, or —$(CH_2CH_2O)_{1-10}CH_3$ (e.g., —$(CH_2CH_2O)_5CH_3$, etc.). In some embodiments the acridan has the structure of formula (A2):

(A2)

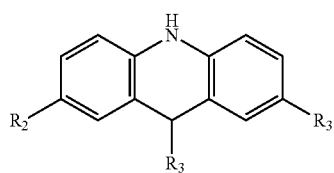

In certain embodiments, the acridan has the structure of formula (A3):

(A3)

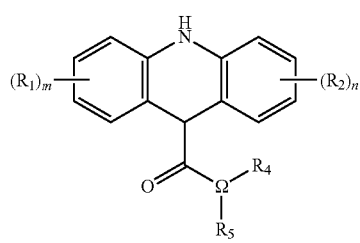

wherein Ω is O or N;

$R_4$ is absent when Ω is O or hydrogen or a $C_1$-$C_{40}$ (e.g., $C_1$-$C_{30}$, $C_1$-$C_{20}$, $C_1$-$C_{10}$, $C_5$-$C_{15}$, $C_5$-$C_{40}$) hydrocarbon radical optionally substituted with one or more (e.g., 1-15) heteroatoms (e.g., O, S, N, P, F, Cl, Br, I), thereof and wherein $R_4$ and $R_5$ may optionally comprise a zwitterionic group (e.g. —Z) and/or a zwitterionic linker group (e.g., —$Z^L$—); and $R_5$ hydrogen or a $C_1$-$C_{40}$ hydrocarbon radical optionally substituted with one or more (e.g., 1-15) heteroatoms (e.g., O, S, N, P, F, Cl, Br, I), and combinations thereof and wherein $R_4$ and $R_5$ may optionally comprise a zwitterionic group (e.g. —Z) and/or a zwitterionic linker group (e.g., —$Z^L$—). The zwitterionic linker-$Z^L$— may have the structure:

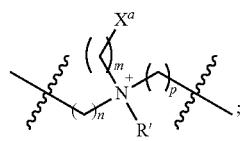

wherein "m" is 0 (i.e. it is a bond) or 1;

"n" and "p" are independently at each occurrence an integer from 0 (i.e. it is a bond) to 10;

$X^a$ is an anionic group; and

R' is hydrogen or lower alkyl (e.g., is methyl, ethyl, propyl, isopropyl, butyl, isobutyl, pentyl, etc.).

In preferred embodiments, acridan has the structure of formula (A4):

(A4)

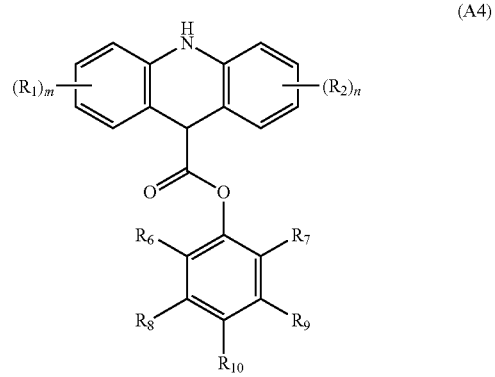

wherein $R_6$-$R_{10}$ are independently selected from hydrogen or a $C_1$-$C_{25}$ (e.g., $C_1$-$C_{20}$, $C_1$-$C_{10}$, $C_5$-$C_{15}$, $C_5$-$C_{25}$) hydrocarbon radical (e.g., alkyl such as methyl, ethyl, or propyl, alkoxy such as methoxy, ethoxy, propoxy, or isopropoxy) optionally substituted with one or more (e.g., 1-15) heteroatoms (e.g., O, S, N, P, F, Cl, Br, I), and wherein $R_6$-$R_{10}$ may optionally comprise a zwitterionic group (e.g. —Z) and/or a zwitterionic linker group (e.g., —$Z^L$—). Typically, at least one of $R_6$-$R_{10}$ is not hydrogen. In some embodiments, $R_6$ and $R_7$ are alkyl (e.g., methyl). In some embodiments, at least one of $R_6$-$R_{10}$ comprises a leaving group for forming a conjugate with an analyte, analyte analog, or binding partner for an analyte. In some embodiments, at least one of $R_6$-$R_{10}$ is alkoxy. In preferred embodiments, the acridan has the structure of formula (A5), (A6), or (A7):

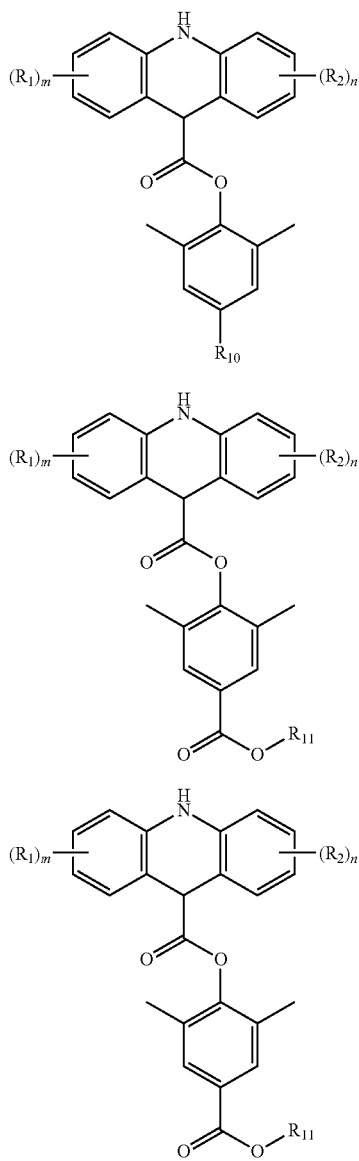

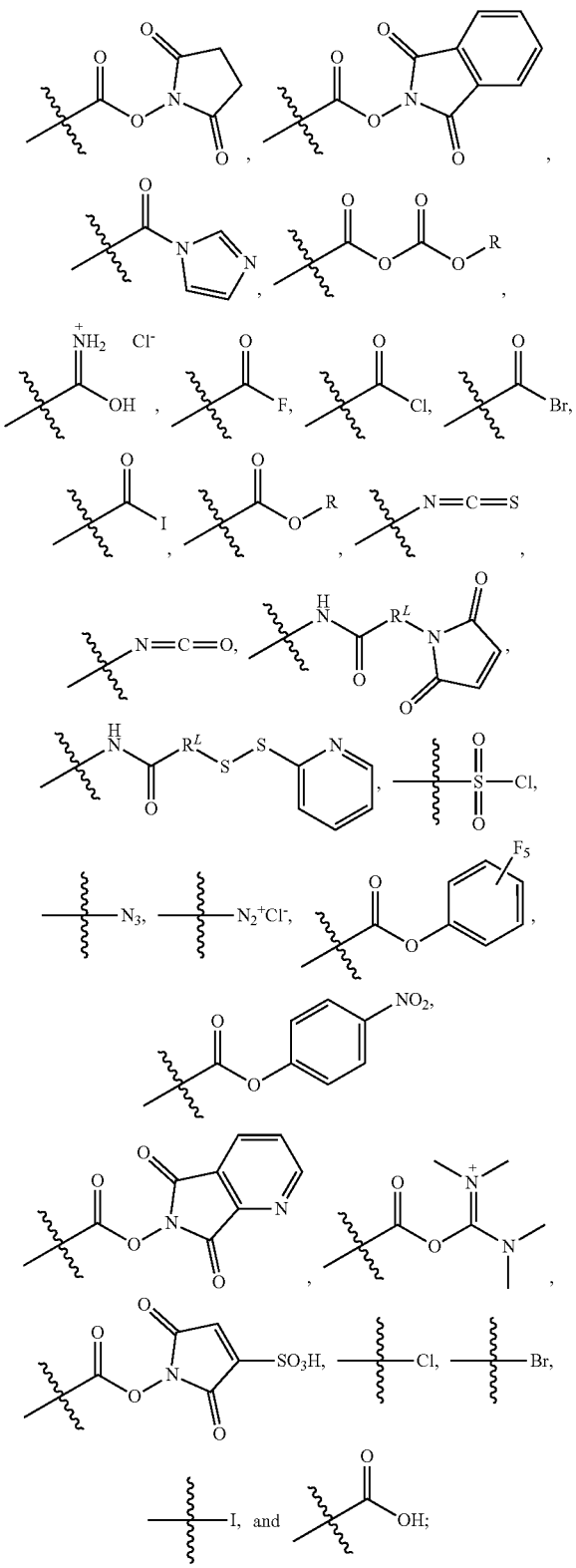

In some embodiments, $R_6$-$R_{12}$ may comprise a leaving group for forming a conjugate with an analyte, analyte analog, or binding partner for an analyte. For example, $R_6$-$R_{12}$ may comprise a group L selected from:

wherein $R_{11}$ is alkyl, alkenyl, alkynyl, or aralkyl optionally substituted with one or more (e.g., 1-15) heteroatoms (e.g., O, S, N, P, F, Cl, Br, I).

The acridan may also have the structure of formula (A8):

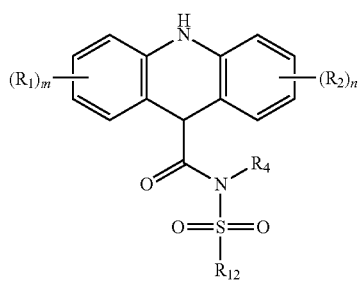

wherein $R_{12}$ is a $C_1$-$C_{20}$ hydrocarbon (e.g., methyl, etc.).

wherein R is independently at each occurrence hydrogen or a $C_1$-$C_{10}$ hydrocarbon (e.g., alkyl, alkenyl, alkynyl, aryl, arylalkyl); and $R_L$ is a bivalent $C_1$-$C_{10}$ hydrocarbon (e.g., alkyl, alkenyl, alkynyl, aryl, arylalkyl). In preferred embodiments, $R_6$-$R_{12}$ are selected from hydrogen, alkyl, —C(O)OH, —C(O)alkoxy, and alkoxy.

In some embodiments, the acridan may be produced by reducing the corresponding acridine. For example an acridine having the structure

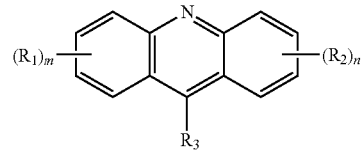

may be reduced to form an acidan having the structure of formula (A1). Similar corresponding acridines may be reduced to form acridans having the structure of formulas (A1)-(A8). In one embodiment, the acridine ester has the formula:

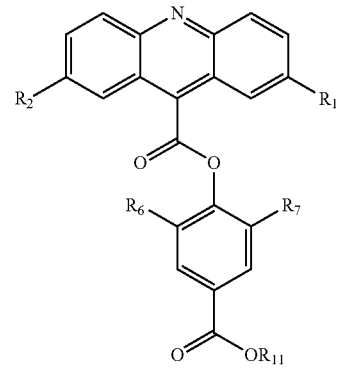

wherein one of $R_1$ or $R_2$ is hydrogen or OR and the other of $R_1$ or $R_2$ is OR;

$R_6$, $R_7$, and $R_{11}$ are R; and

R is independently at each occurence a $C_1$-$C_{40}$ (e.g., $C_1$-$C_{30}$, $C_1$-$C_{20}$, $C_1$-$C_{10}$, $C_5$-$C_{15}$, $C_5$-$C_{40}$) hydrocarbon radical (e.g., alkyl, alkenyl, alkynyl, aryl, aralkyl) optionally substituted with 1-20 heteroatoms (e.g., O, S, N, P, F, Cl, Br, I). In other embodiments, $R_1$ and $R_2$ are both OR. In certain embodiments, $R_6$ and $R_7$ are methyl groups and $R_{11}$ is selected from methyl, ethyl, or isopropyl groups. In some embodiments, $R_1$ and $R_2$ are selected from lower alkoxy, and $R_6$, $R_7$ and $R_{11}$ are lower alkyl.

Preferred reducing reagents for the conversion of acridine to the acridan prior to N-alkylation are hydride reducing agents selected from picoline-borane, sodium borohydride, lithium borohydride, potassium borohydride, sodium cyanoborohydride or potassium cyanoborohydride, Alternatively, catalytic hydrogenation over a metal catalyst selected from palladium or platinum on carbon can be used for the reduction.

The N-alkylated acridan may have the structure according to formula (NA1):

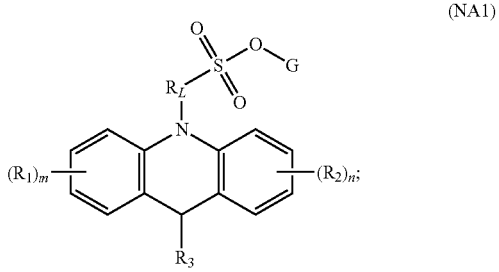

wherein $R_1$ and $R_2$ are independently selected from electron donating groups;

$R_3$ is hydrogen or a $C_1$-$C_{45}$ hydrocarbon radical optionally substituted with one or more (e.g., 1-20) heteroatoms (e.g., O, S, N, P, F, Cl, Br, I) and wherein $R_3$ may optionally comprise a zwitterionic group (e.g. —Z) and/or a zwitterionic linker group (e.g., —$Z^L$—);

—$R_L$— is independently selected at each occurrence from $C_{1-20}$ linear or branched bivalent hydrocarbon radicals; optionally substituted with one or more (e.g., 1-5) heteroatoms (e.g., O, S, N, P, F, Cl, Br, I, etc.), and combinations thereof, and wherein $R_L$ optionally comprises a zwitterionic linker group (e.g., —$Z^L$—); and G is an acid-labile protecting group. These intermediate compounds are useful in the synthesis of chemiluminescent acridinium compounds. Preferably, $R_L$ is lower alkyl.

Following N-alkylation of the acridan, the N-alkylated acridan may be reduced to a protected N-alkylacridinium compound. In some embodiments, the protected N-alkylacridinium has the structure:

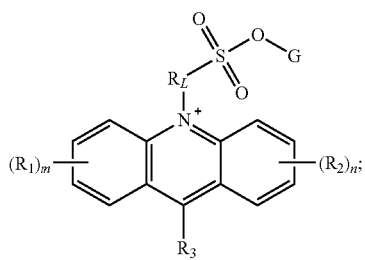

wherein "m" and "n" are independently 0-4 and at least one of "m" or "n" is greater than 0;

$R_1$ and $R_2$ are independently selected from electron donating groups;

$R_3$ is hydrogen or a $C_1$-$C_{45}$ hydrocarbon radical optionally substituted with one or more (e.g., 1-20) heteroatoms (e.g., O, S, N, P, F, Cl, Br, I) and wherein $R_3$ may optionally comprise a zwitterionic group (e.g. —Z) and/or a zwitterionic linker group (e.g., —$Z^L$—);

—$R_L$— is independently selected at each occurrence from $C_{1-20}$ linear or branched bivalent hydrocarbon radicals; optionally substituted with one or more (e.g., 1-5) heteroatoms (e.g., O, S, N, P, F, Cl, Br, I, etc.), and combinations thereof, and wherein $R_L$ optionally comprises a zwitterionic linker group (e.g., —$Z^L$—); and G is an acid-labile protecting group.

An oxidation reaction of the N-alkylacridan may be used to produce acridinium compounds. In some embodiments, the oxidation occurs in an air environment. In other embodiment, oxidation of the N-alkylated acridan may be achieved with molecular oxygen or DDQ (2,3-dichloro-5,6-dicyanobenzoquinone). In most embodiments, the protected N-alkylacridinium may then unprotected using a cleavage reaction. However, in other embodiments, the sulfonate is deprotected prior to oxidation of the N-alkylacridan. Typically, the cleavage reaction of the protected sulfonate protecting group occurs in an acid compatible with the N-alkylacridinium reactants. In some embodiments, the acid is a Brönsted acid selected from hydrochloric acid, hydrobromic acid, sulphuric acid, benzenesulphonic acid, p-toluenesulphonic acid (p-TSA), methanesulphonic acid, ethanesulphonic acid, trifluoromethanesulfonic acid (TFMSA), trifluoroacetic acid (TFA), trichloroacetic acid (TCA), dichloroacetic acid (DCA), chloroacetic acid, formic acid and acetic acid. In some embodiments, the acid may be a Lewis acid or a silicon compound or a combination of two or more such acids and/or silicon compounds. The acid may be selected from boron trifluoride, boron trichloride, boron tribromide, aluminium chloride, tin chloride, titanium chloride, silicon tetrachloride, chlorotrimethylsilane Me3SiCl (TMSCl), bromotrimethylsilane Me3SiBr (TMSBr) and trimethylsilyl trifluoromethanesulphonate (TMSOTf). In some embodiments, the acid for cleavage of the sulfonate protecting group may be trifluoroacetic acid (TFA), hydrochloric acid, or sulfuric acid etc. In preferred embodiments, the acid is TFA.

Preferred solvents for any reaction (e.g., reduction, N-alkylation, oxidation, cleavage of protecting group or combinations thereof) are common organic solvents such as dichloromethane, chloroform, acetonitrile, toluene, etc. In some embodiments, the N-alkylation occurs in anhydrous dichloromethane at room temperature under inert atmosphere (e.g., Argon).

Methods for the synthesis of N-alkylated acridiniums are provided which may comprise:
(a) reducing an acridine compound to convert said acridine compound to an acridan;
(b) N-alkylating said acridan according to the method of any one of claims 1-20 to produce an N-alkylacridan; and
(c) oxidizing said N-alkylacridan to convert said N-alkylacridan to said acridinium.

In some embodiments, the method further comprises cleaving the acid-labile protecting group. In some embodiments, the acid-labile protecting group is cleaved from the acridinium (i.e., to produce an unprotected N-alkylacridinium) by acid hydrolysis following said N-alkylation step. In most embodiments, the cleaving may occur after the oxidizing step.

In some embodiments, the methods of the synthesis of chemiluminescent acridinium compounds comprises:
(a) reducing an acridine compound having the structure:

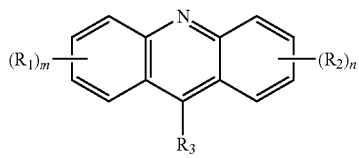

to produce an acridan having the structure:

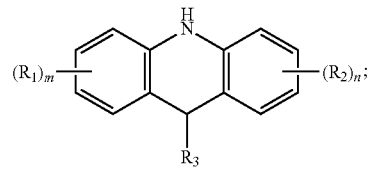

(b) reacting said acridan with a first protected sodium triflate compound having the structure:

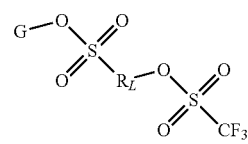

to produce an N-alkylacridan having the structure:

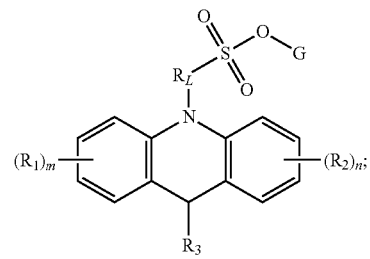

and
(c) oxidizing said N-alkylacridan to produce an N-alkylacridinium having the structure:

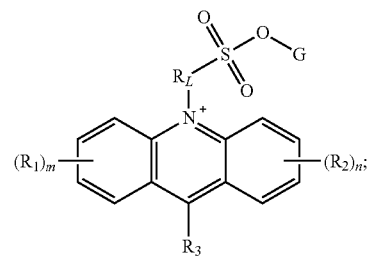

wherein "m" and "n" are independently 0-4 and at least one of "m" or "n" is greater than 0;
$R_1$ and $R_2$ are independently selected from electron donating groups;
$R_3$ is hydrogen or a $C_1$-$C_{45}$ hydrocarbon radical optionally substituted with one or more (e.g., 1-20) heteroatoms (e.g., O, S, N, P, F, Cl, Br, I) and wherein $R_3$ may optionally comprise a zwitterionic group (e.g. —Z) and/or a zwitterionic linker group (e.g., —$Z^L$—);
—$R_L$— is independently selected at each occurrence from $C_{1-20}$ linear or branched bivalent hydrocarbon radicals; optionally substituted with one or more (e.g., 1-5) heteroatoms (e.g., O, S, N, P, F, Cl, Br, I, etc.), and combinations thereof, and wherein $R_L$ optionally comprises a zwitterionic linker group (e.g., —$Z^L$—); and
G is an acid-labile protecting group.

In some embodiments, the acridine has the structure

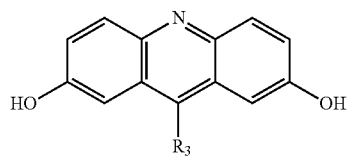

and said method further comprises reacting said acridine prior to said reducing step with a second protected sulfonate triflate prior to acridine reduction having the structure

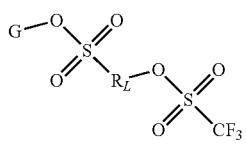

to produce an acridine having the structure

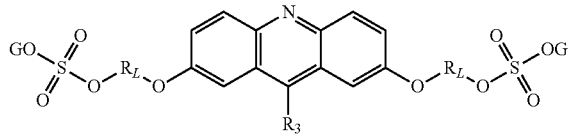

These methods may produce an N-alkylacridinium with the structure:

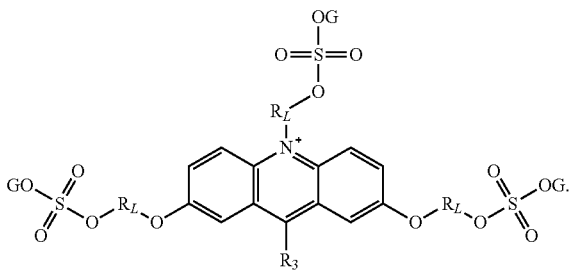

wherein the protecting group on the N-alkylated functional group may be the same or different as the protecting group on the O-alkylated functional groups.

In some embodiments, the acid-labile protecting groups may be removed to produce an acridinium compound having the structure:

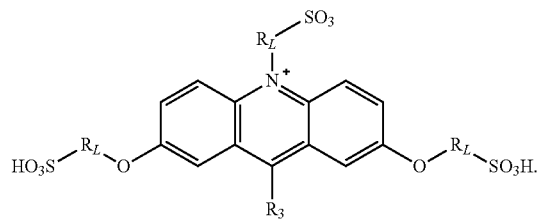

EXAMPLES

The following Examples illustrate the synthesis of a representative number of acridan and acridinium compounds. Accordingly, the Examples are intended to illustrate but not to limit the disclosure. Additional compounds not specifically exemplified may be synthesized using conventional methods in combination with the methods described herein.

The following examples describe the syntheses of compounds 5, 6 and 7 using the methods of the present invention. These compounds are advanced precursors to the acridinium esters 1-4.

Example 1: Synthesis of Compound 5

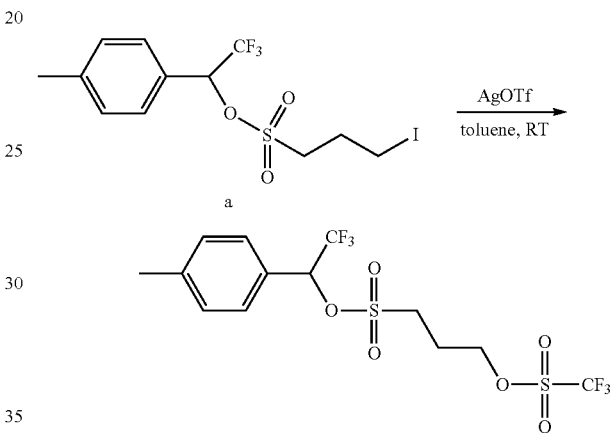

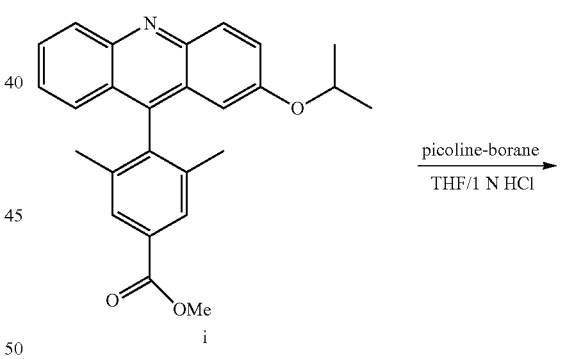

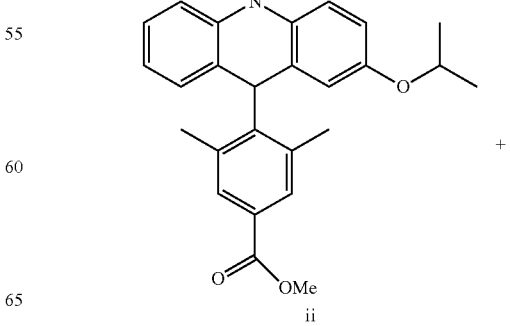

35
-continued

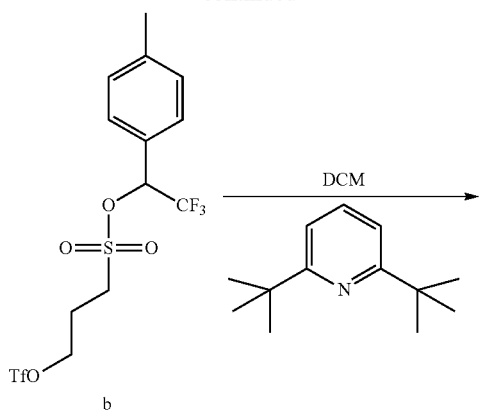

b

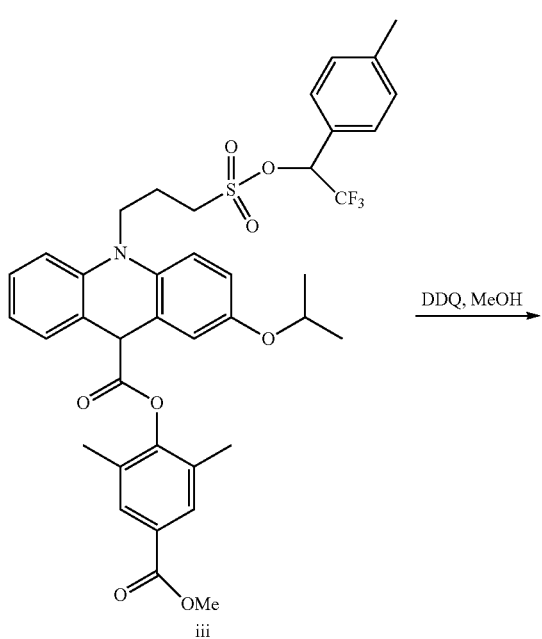

iii

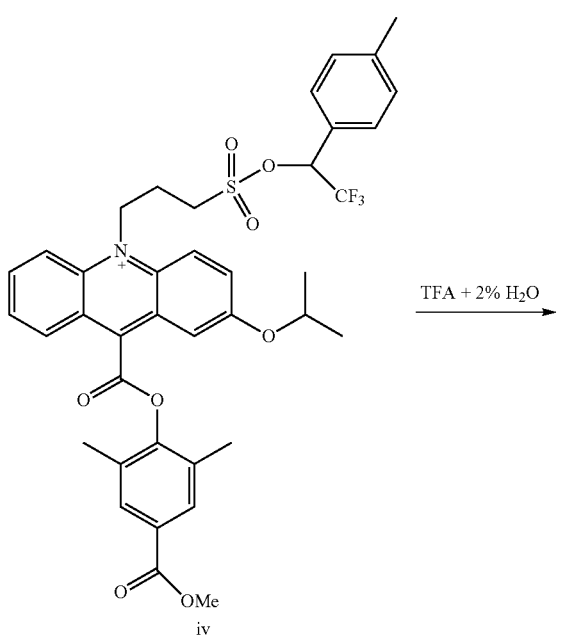

iv

36
-continued

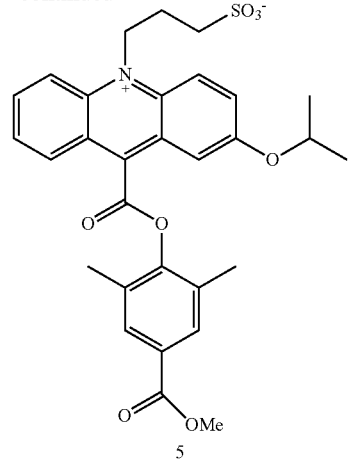

5

Reduction: A solution of 2-isopropoxyacridine methyl ester, compound i (Natrajan et al, Org. Biomol. Chem. 10 (2012): 3432-3447) (0.1 g, 0.225 mmole) was dissolved in a mixture of tetrahydrofuran (THF, 9 mL) and 1 N HCl (1 mL). To this yellow solution was added solid picoline-borane complex (29 mg, 1.2 equivalents). The reaction was stirred at room temperature for 2 hours by which time the color of the reaction mixture had faded to a light yellow color. HPLC analysis using a Phenomenex bondclone $C_{18}$, 3.9×30 mm column and a 30 minute gradient of 10→100% MeCN/water (each with 0.05% TFA) at a flow rate of 1 mL/minute and UV detection at 260 and 220 nm showed product 2-isopropxyacridan methyl ester ii eluting at 22.8 minutes with very little starting material i eluting at 23.8 minutes. The reaction was concentrated under reduced pressure to remove the THF and the residual aqueous layer was diluted with ethyl acetate (25 mL) which was subsequently washed with 5% aqueous sodium bicarbonate solution followed by 5% aqueous NaCl. The ethyl acetate solution was dried over anhydrous magnesium sulfate, filtered and concentrated under reduced pressure to give compound ii as a light yellow solid. Yield=116 mg (quantitative). This material was used as such for the N-alkylation reaction.

N-Alkylation: A solution of 2-isopropoxyacridan methyl ester (compound ii) (0.1 g, 0.225 mmole), triflate b (0.686 g, 0.00155 mole), and 2,6-di-tert-butylpyridine (0.1 mL, 0.450 mmole) was stirred in anhydrous dichloromethane (2-3 mL) at room temperature under an argon atmosphere (balloon) protected from light for a week. TLC analysis (1:4, ethyl acetate/hexanes) showed complete conversion to a less polar product. HPLC analysis as described above showed product eluting at 26.8 minutes. The reaction was concentrated under reduced pressure and the product iii was purified by flash chromatography on silica using ethyl acetate/hexanes. Yield=107 mg (64%, sticky solid). MALDI-TOF MS 738 observed.

The protected sulfopropyl iodide compound a was synthesized using a literature procedure (Pauff and Miller, J. Org. Chem., 2013, 78, 711-716). A solution of compound a (0.775 g, 0.00184 mole) in anhydrous toluene (10 mL) was treated with silver trifluoromethane sulfonate (0.47 g, 0.00184 mole). The reaction was stirred at room temperature under a nitrogen atmosphere protected from light. After 16 hours, a yellow precipitate had formed in the reaction. The reaction was diluted with ethyl acetate (25 mL) and was filtered. The filtrate was washed with cold water and then aqueous 5% NaCl (25 mL each). It was then dried over anhydrous magnesium sulfate and concentrated under reduced pressure to give a light brown oil which was used as such for the next reaction. Yield=0.686 g (compound b, 84%).

Oxidation: A solution of the N-alkylated acridan ester (compound iii) (66 mg, 0.089 mmole) in methanol (5 mL) was treated with DDQ (24.3 mg, 0.0089 mmole). The reaction was stirred at room temperature. After 30 minutes, HPLC analysis as described above showed complete conversion to the acridinium ester eluting at 22 minutes. The solvent was removed under reduced pressure.

Deprotection: The residue was stirred in TFA (1 mL) and water (0.02 mL) at room temperature. After 1 hour, HPLC analysis showed complete conversion to the product 5 eluting at 17.3 minutes. The reaction was diluted with methanol (5 mL) and concentrated under reduced pressure. A similar series of reactions where the oxidation was performed first on compound iii followed by de-blocking of the sulfonate protecting group to give crude 5 was also successful. The combined crude product 5 from these reactions (starting from 100 mg of 2-isopropxyacridan ii) was purified by flash chromatography on silica using ethyl acetate/methanol. The product was isolated in excellent purity as illustrated in FIG. 1. Yield=37 mg (46% from iii, two steps).

Example 2: Synthesis of Compound 6

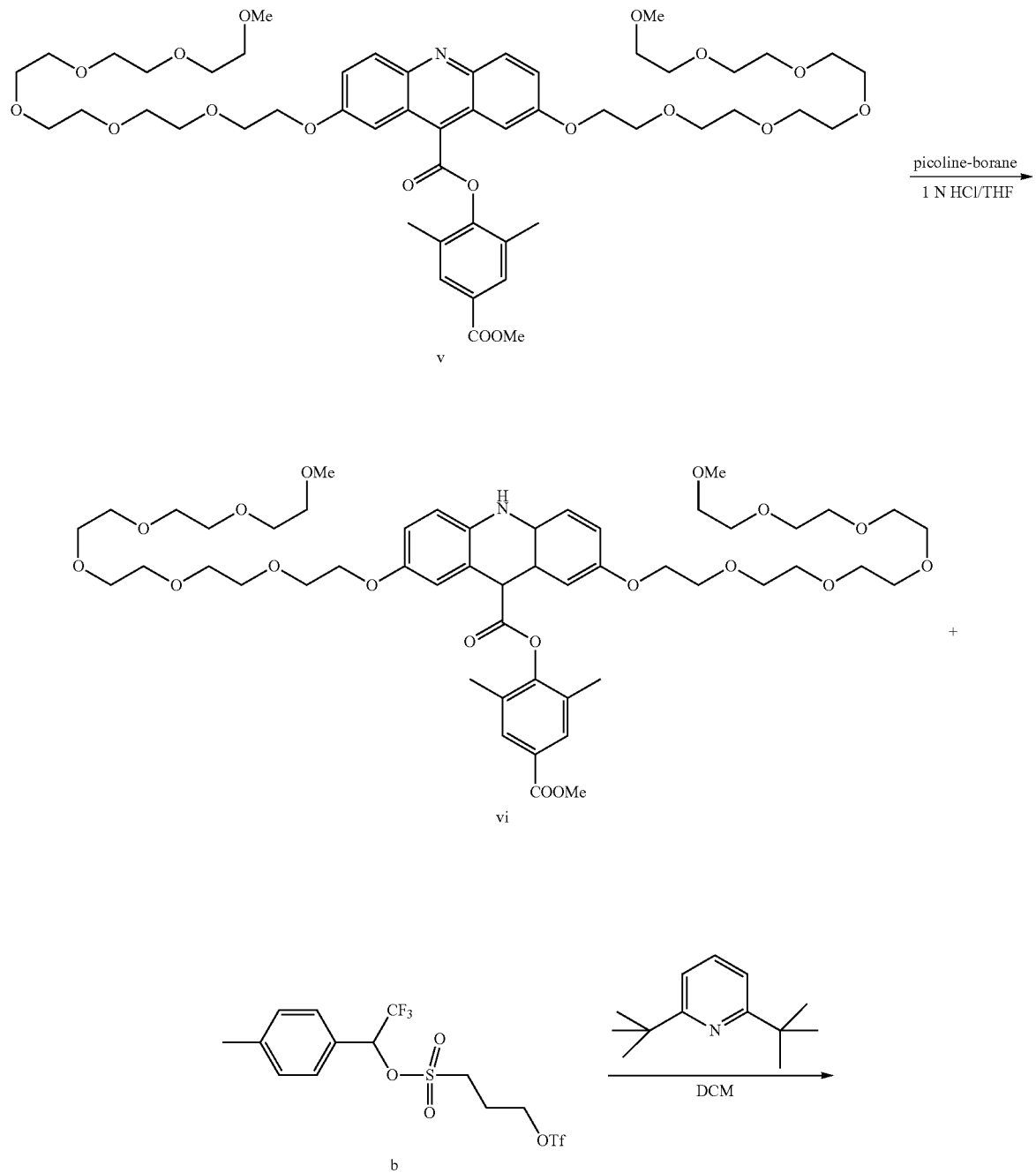

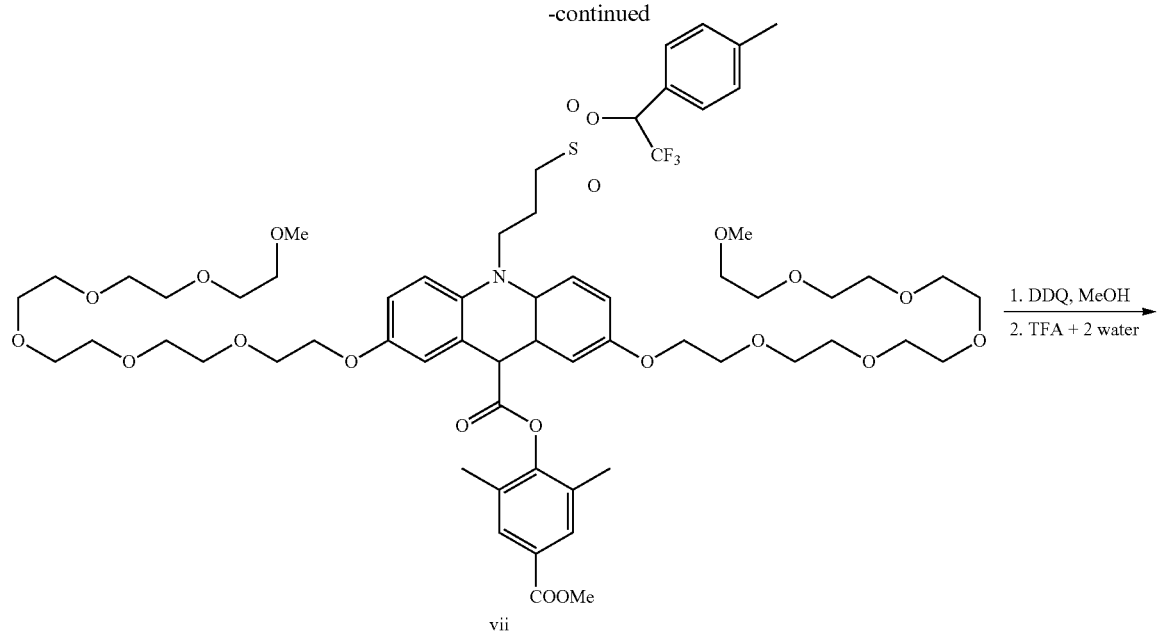

Reduction: The PEG acridine ester (compound v) precursor to acridan vi has been described previously (U.S. Pat. No. 7,309,615, hereby incorporated by reference in its entirety and specifically in relation to acridinium esters and their synthesis). Compound v (95 mg, 0.098 mmole) was dissolved in THF (9 mL) and 1N HCl (1 mL). Picoline borane (21 mg, 2 equivalents) was added in one portion and the reaction was stirred at room temperature. After 4 hours, the initial dark yellow solution had faded to a light yellow color. HPLC analysis of the reaction as described previously showed acridan product vi eluting at 18.7 minutes with very little starting material at 21 minutes. The reaction was then concentrated under reduced pressure to remove the THF and the aqueous residue was partitioned between ethyl acetate (25 mL) and cold 1N HCl (25 mL). The ethyl acetate layer was separated and was washed successively with aqueous 5% ammonium chloride, 5% sodium bicarbonate and 5% NaCl. It was then dried over anhydrous magnesium sulfate, filtered and concentrated under reduced pressure. The acridan vi was recovered as a white, sticky solid. Yield=90 mg (95%)

N-alkylation: A solution of acridan vi (90 mg, 0.092 mmole), triflate b (0.45 g, 1 mmole) and 2,6-di-tert-butylpyridine (0.04 mL, 2 equivalents) in dichloromethane (3 mL) was stirred under an inert atmosphere of nitrogen (balloon), protected from light at room temperature for a week. HPLC analysis of the reaction mixture showed >90% conversion to the N-alkylated acridan vii eluting at 22.5 minutes. The reaction was concentrated under reduced pressure. The product was purified by flash chromatography on silica using a mixture of ethyl acetate and methanol. Yield=0.1 g (85%, sticky solid), MALDI TOF MS 1268 observed.

Oxidation: A solution of the N-alkylated acridan vii (0.1 g, 0.078 mmole) in methanol (10 mL) was treated with DDQ (18 mg, 1 equivalent). The reaction was stirred at room temperature. After 30 minutes, HPLC analysis showed complete oxidation to the acridinium ester eluting at 20.2 minutes.

Figure 2:
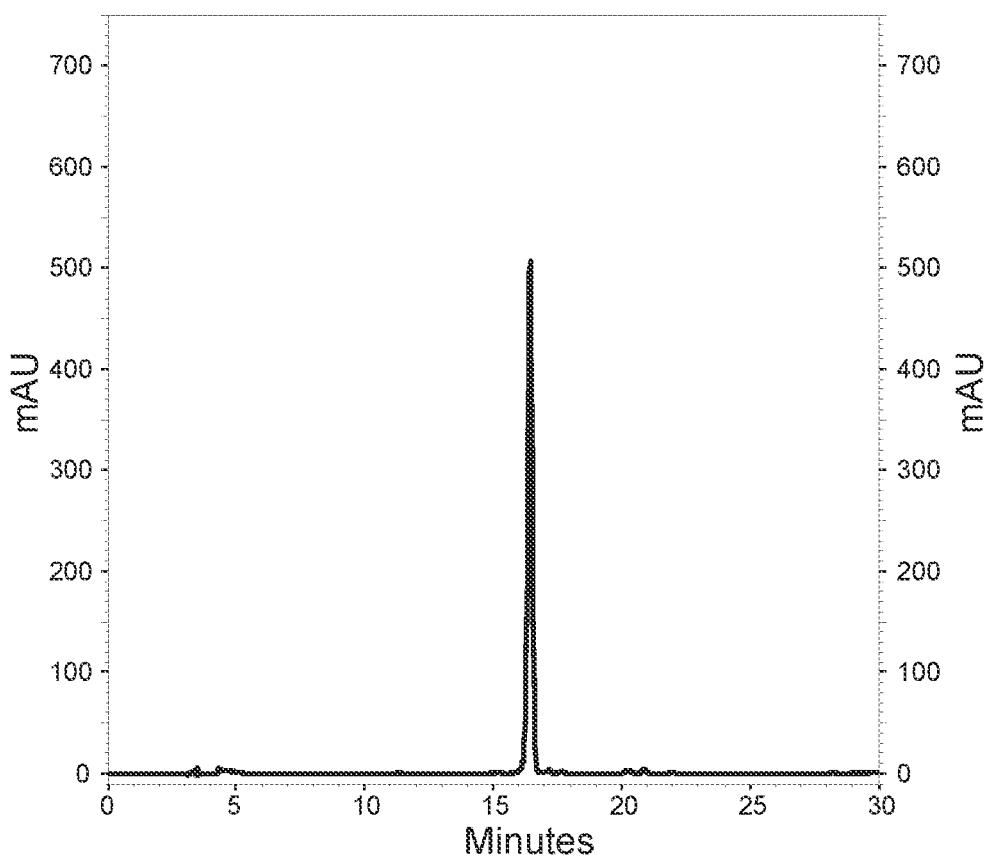
FIG. 2 is an HPLC trace of N-sulfopropyl PEG acridinium ester (Compound 6) synthesized using the methods of the current invention.

Deprotection: The solvent was then removed under reduced pressure and the acridinium ester was stirred in TFA (1 mL) with water (0.02 mL) at room temperature. After one hour, HPLC analysis showed >90% conversion to the product 6 eluting at 16.5 minutes. The reaction was treated with hexanes (30 mL) to precipitate the product. The hexanes were decanted and the residue was rinsed with hexanes (2×15 mL). The product was then dried under reduced pressure and then purified by flash chromatography on silica using ethyl acetate/methanol. FIG. 2 shows the HPLC trace of product 6 obtained following this synthesis. Yield=46 mg (50%). MALDI TOF MS 1097 observed.

Example 3: Synthesis of Compound 7

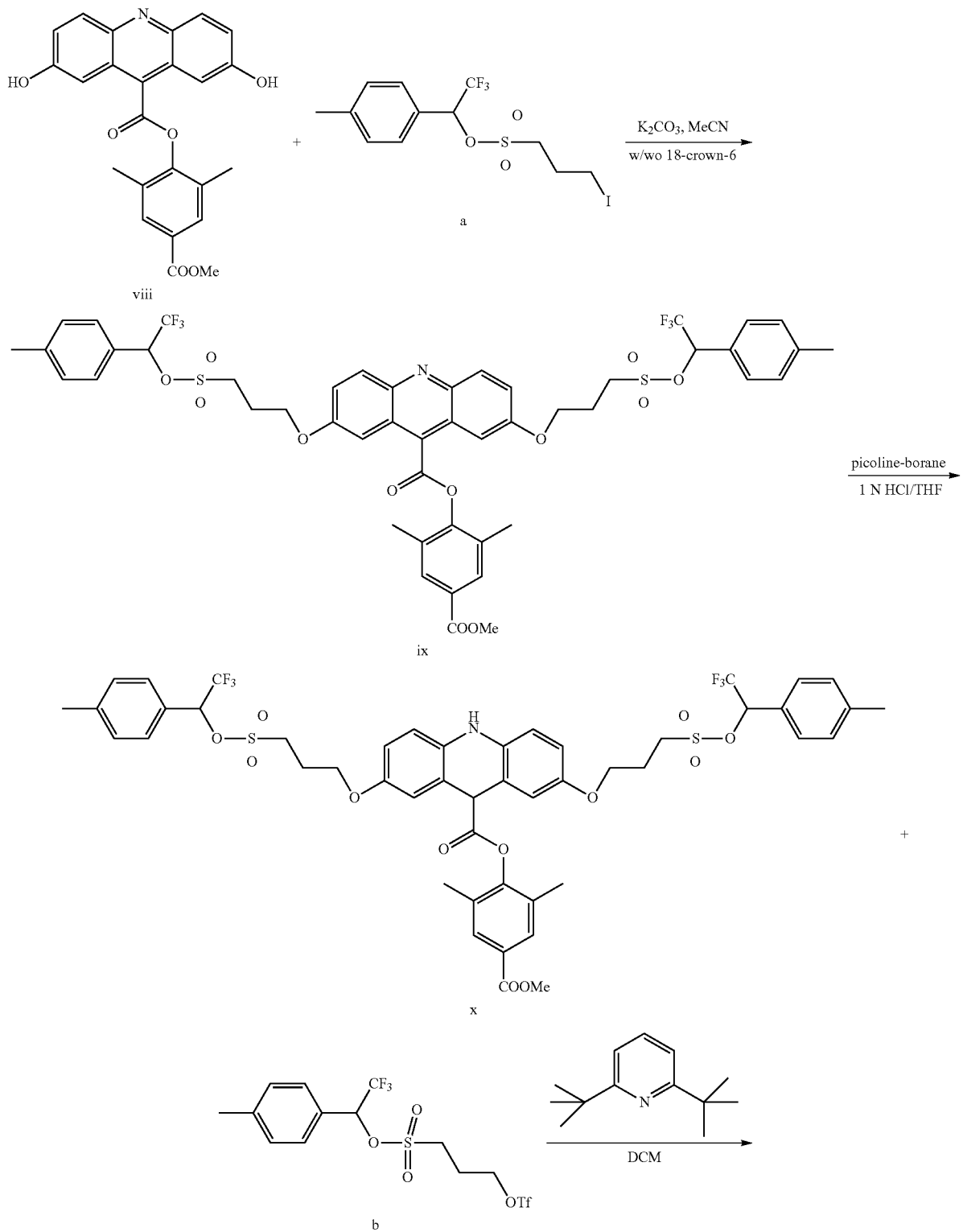

-continued
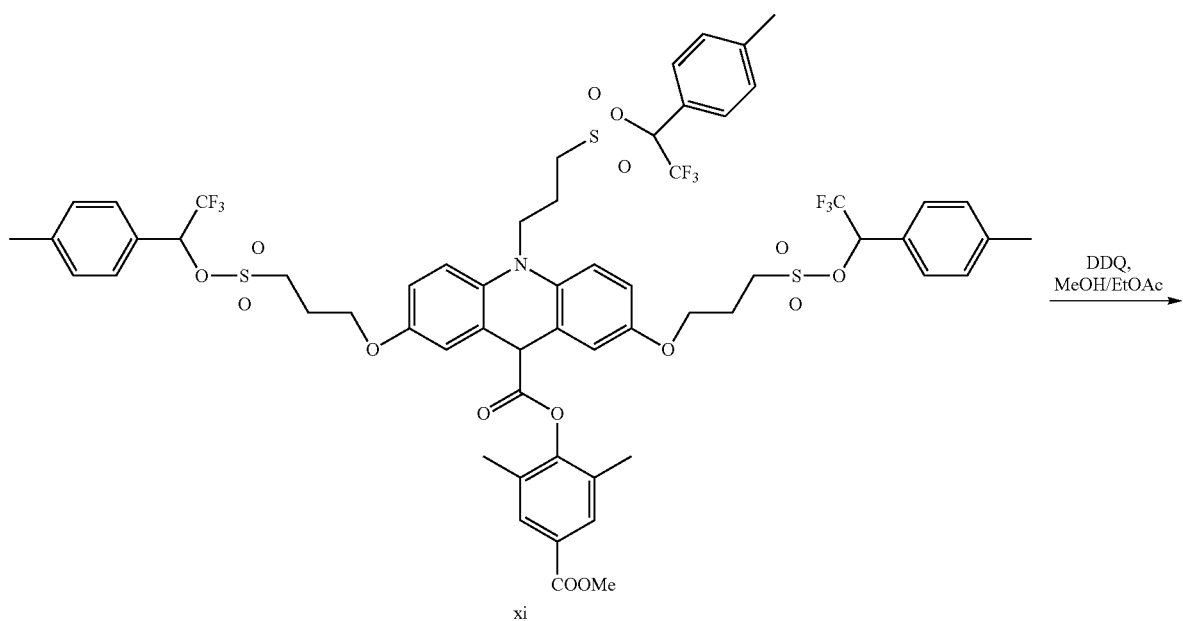
xi
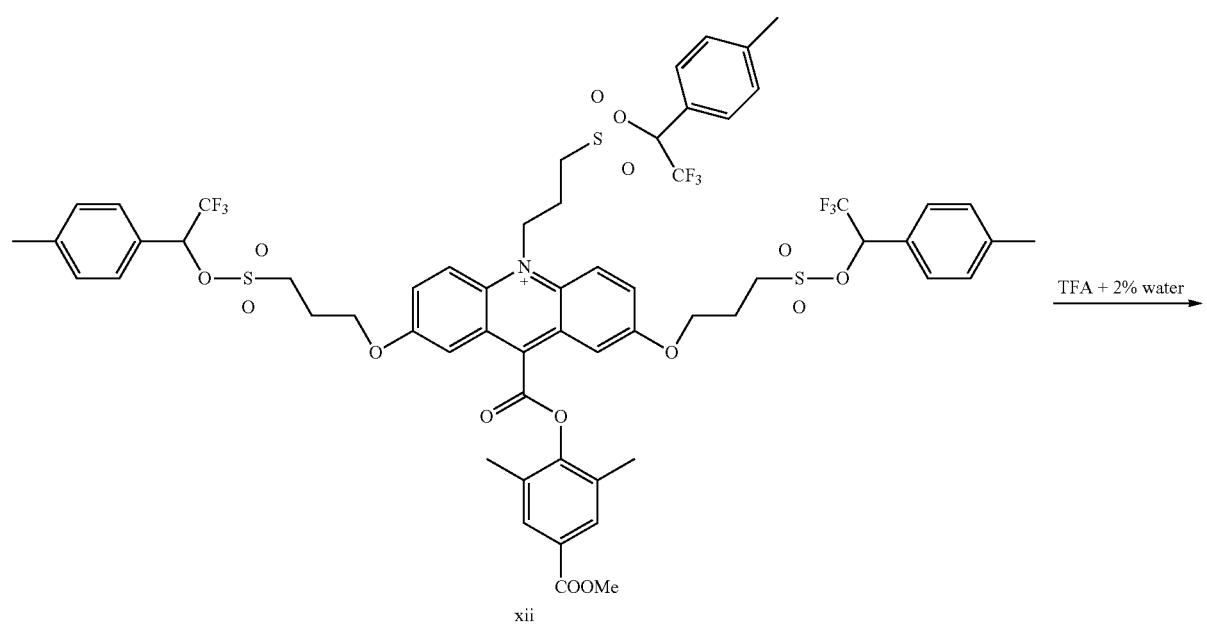
xii

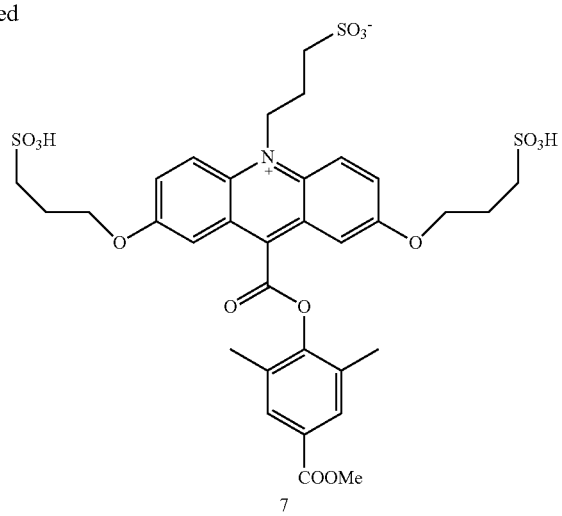

7

A mixture of compound viii (U.S. Pat. No. 7,309,615, hereby incorporated by reference in its entirety and specifically in relation to acridinium esters and synthesis thereof) (50 mg, 0.12 mmole), potassium carbonate anhydrous (36 mg, 2.2 equivalents), 18-crown-6 (1,4,7,10,13,16-hexaoxacyclooctadecane) (70 mg, 2.2 equivalents) was treated with a MeCN solution (10 mL) of iodide a (127 mg, 2.5 equivalents). The reaction was heated at 85° C. in an oil bath. The initial dark red solution faded away to a light brown color after 3 hours. HPLC analysis as described previously showed the formation of a major product eluting at 28 minutes. The reaction was cooled to room temperature and concentrated under reduced pressure. A similar scale reaction but without the addition of crown ether afforded a similar reaction profile but product formation required heating for 6 hours. The crude product from both reactions were combined and purified by flash chromatography on silica using a mixture of ethyl acetate/hexanes. Yield=0.1 g (42%). MALDI TOF MS 1006.4 observed.

Reduction: A solution of acridine ester ix (0.1 g, 0.096 mmole) in THF (18 mL) and 1N HCl (2 mL) was treated with solid picoline borane (21.3 mg, 2 equivalents). The reaction was stirred at room temperature for 12 hours. HPLC analysis showed acridan x eluting at 26.3 minutes with very little starting material at 28 minutes. The THF was removed under reduced pressure and the residue was partitioned between cold 1N HCl (25 mL) and ethyl acetate (50 mL). The ethyl acetate extract was washed successively with 25 mL each of aqueous 5% ammonium chloride, 5% sodium bicarbonate and 5% sodium chloride. It was then dried over anhydrous magnesium sulfate, filtered and concentrated under reduced pressure. Crude Yield=0.13 g. This material was used such for the N-alkylation reaction.

N-alkylation: The acridan compound x (0.13 g crude, 0.1 mmole) was dissolved in anhydrous dichloromethane (4 mL) and treated with triflate b (0.43 g, 0.97 mmole) and 2,6-di-tert-butylpyridine (0.057 mL, 2.5 equivalents). The reaction was stirred under an inert nitrogen atmosphere at room temperature for a week. HPLC analysis showed ~80% conversion to product xi eluting at 28.3 minutes. (A similar reaction performed on a 44 mg scale of acridan x showed complete conversion to product after two weeks.) The reaction was concentrated under reduced pressure and the product was purified by flash chromatography on silica using a mixture of ethyl acetate and hexanes. Yield=73 mg (56%). MALDI TOF MS 1300 observed.

Oxidation: A solution of the N-alkylated acridan xi (73 mg, 0.056 mmole) in 1:1 methanol/ethyl acetate (10 mL) was treated with DDQ (14 mg, 1.1 equivalents). The reaction was stirred at room temperature. After 10 minutes, HPLC analysis showed complete conversion to the acridinium ester eluting at 25 min.

Deprotection: The solvent was removed under reduced pressure and the residue was stirred in TFA (2 mL) and water (0.04 mL). After 1.5 hours, HPLC analysis showed a major product compound 6 eluting at 11.3 minutes. The solvent was removed under reduced pressure and the residue was rinsed with ether (50 mL) followed by 1:1 ether/hexanes and then 1:1 hexanes/ethyl acetate. The crude product was then dried under reduced pressure. Crude Yield=60 mg. MALDI TOF MS 784 observed.

All references including patent applications and publications cited herein are incorporated herein by reference and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:
1. A method for the N-alkylation of an acridan compound comprising reacting said acridan compound with a protected sulfonate triflate compound having the structure of formula (R1):

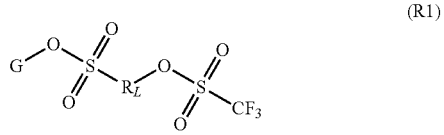

(R1)

wherein G is an acid-labile protecting group; and

—R$_L$— is a C$_{1-20}$ linear or branched bivalent hydrocarbon radicals; optionally substituted with one or more heteroatoms, and combinations thereof, and wherein R$_L$ optionally comprises a zwitterionic linker group;

wherein said acridan has the structure of formula (A1):

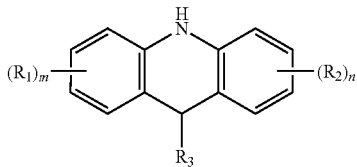

(A1)

wherein "m" and "n" are independently 0-4 and at least one of "m" or "n" is greater than 0;

R$_1$ and R$_2$ are independently selected from electron donating groups; and

R$_3$ is hydrogen or a C$_1$-C$_{45}$ hydrocarbon radical optionally substituted with one or more heteroatoms and wherein R$_3$ may optionally comprise a zwitterionic group and/or a zwitterionic linker group.

2. The method according to claim 1, wherein said sulfonate triflate compound has the structure of formula (R2):

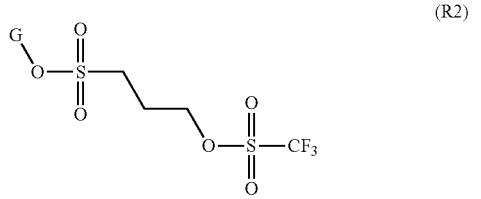

(R2)

3. The method according to any one of claims 1-2, wherein G is selected from

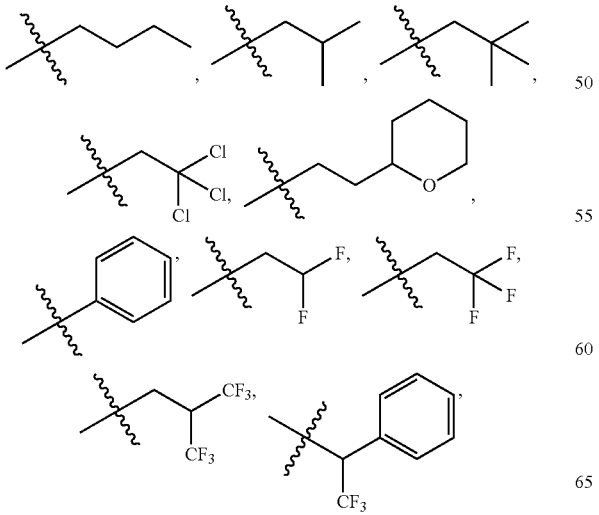

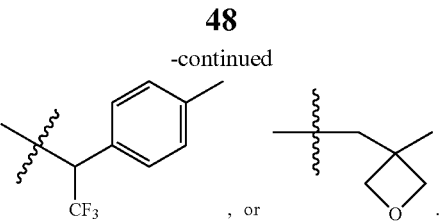

-continued

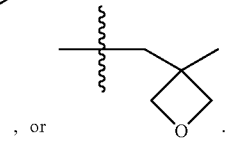

, or

4. The method according to claim 1, wherein said acridan has the structure of formula (A3):

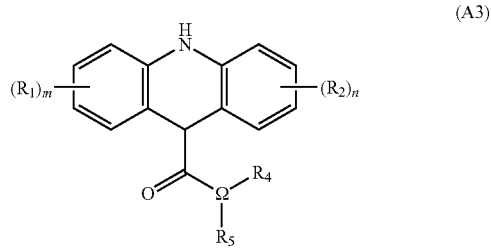

(A3)

wherein Ω is O or N;

R$_4$ is absent when Ω is O or hydrogen or a C$_1$-C$_{40}$ hydrocarbon radical optionally substituted with one or more heteroatoms, and wherein R$_4$ and R$_5$ may optionally comprise a zwitterionic group and/or a zwitterionic linker group; and R$_5$ is hydrogen or a C$_1$-C$_{40}$ hydrocarbon radical optionally substituted with one or more heteroatoms, and wherein R$_4$ and R$_5$ may optionally comprise a zwitterionic group and/or a zwitterionic linker group.

5. The method according to claim 4, wherein said acridan has the structure of formula (A4):

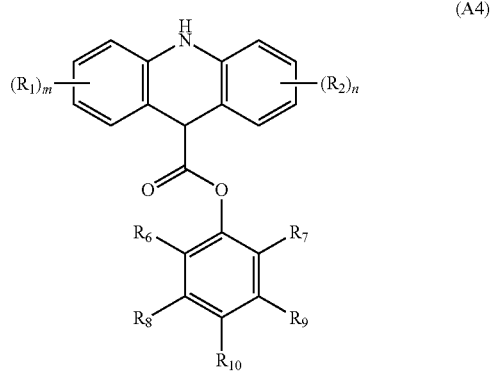

(A4)

wherein R$_6$-R$_{10}$ are independently selected from hydrogen or a C$_1$-C$_{25}$ hydrocarbon radical optionally substituted with one or more heteroatoms, and wherein R$_6$-R$_{10}$ may optionally comprise a zwitterionic group and/or a zwitterionic linker group.

6. The method according to claim 5, wherein at least one of R$_6$-R$_{10}$ comprises a leaving group for forming a conjugate with an analyte, analyte analog, or binding partner for an analyte.

7. The method according to claim 5, wherein said acridan has the structure of formula (A5):

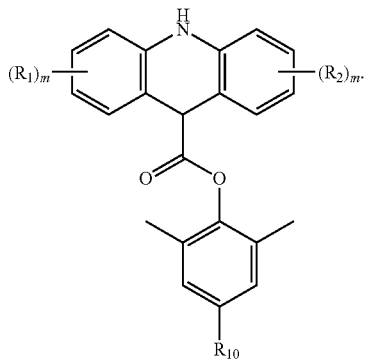

(A5)

8. The method according to claim 4, wherein said acridan has the formula of formula (A8):

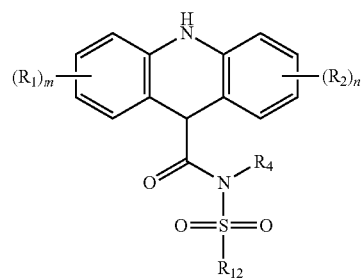

(A8)

wherein $R_{12}$ is hydrogen or a $C_1$-$C_{25}$ hydrocarbon radical optionally substituted with one or more heteroatoms and wherein $R_{12}$ may comprise a zwitterionic group and/or a zwitterionic linker group.

9. A method for the synthesis of an acridinium compound comprising:
(a) reducing an acridine to produce an acridan;
(b) N-alkylating said acridan according to the method of claim 1 to produce an N-alkylacridan;
(c) oxidizing said N-alkylacridan to convert said N-alkylacridan to said acridinium.

10. The method according to claim 9 further comprising cleaving said acid-labile protecting group by acid hydrolysis following said N-alkylation step.

11. The method according to claim 10, wherein said cleaving step occurs after said oxidizing step.

12. The method according to claim 9, wherein said acridine has the structure

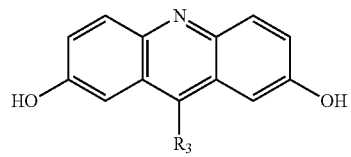

and said method further comprises reacting said acridine, prior to said reducing step, with a second protected sulfonate having the structure

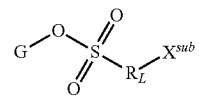

to produce an acridine having the structure

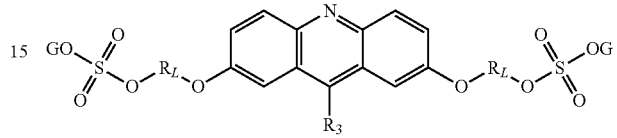

and wherein said N-alkyl acridinium has the structure:

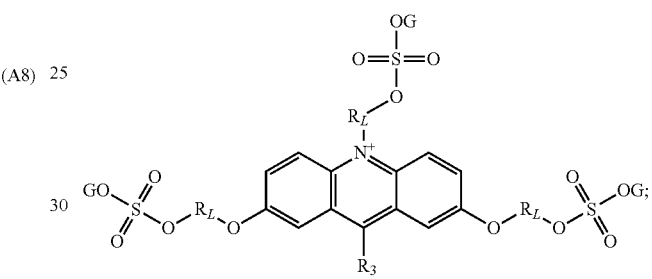

wherein G is independently at each occurrence an acid labile protecting group, $R_L$ is independently at each occurrence a $C_{1-20}$ linear or branched bivalent hydrocarbon radicals; optionally substituted with one or more heteroatoms, and combinations thereof, and wherein $R_L$ optionally comprises a zwitterionic linker group; and
$X^{sub}$ is selected from triflate or halogen.

13. An N-alkylated acridan compound having the structure:

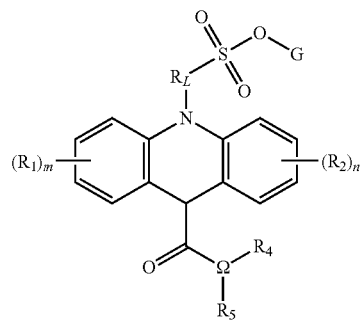

wherein G is an acid-labile protecting group;
"m" and "n" are independently 0-4 and at least one of "m" or "n" is greater than 0;
wherein $\Omega$ is O or N;
—$R_L$—is a $C_{1-20}$ linear or branched bivalent hydrocarbon radicals; optionally substituted with one or more heteroatoms, and combinations thereof, and wherein $R_L$ optionally comprises a zwitterionic linker group;

$R_1$ and $R_2$ are independently selected from electron donating groups;

$R_4$ is absent when Ω is O or hydrogen or a $C_1$-$C_{40}$ hydrocarbon radical optionally substituted with one or more heteroatoms, and wherein $R_4$ and $R_5$ may optionally comprise a zwitterionic group and/or a zwitterionic linker group; and $R_5$ hydrogen or a $C_1$-$C_{40}$ hydrocarbon radical optionally substituted with one or more heteroatoms, and combinations thereof and wherein $R_4$ and $R_5$ may optionally comprise a zwitterionic group and/or a zwitterionic linker group.

14. The N-alkylated acridan according to claim 13, wherein said N-alkylated acridan has the structure:

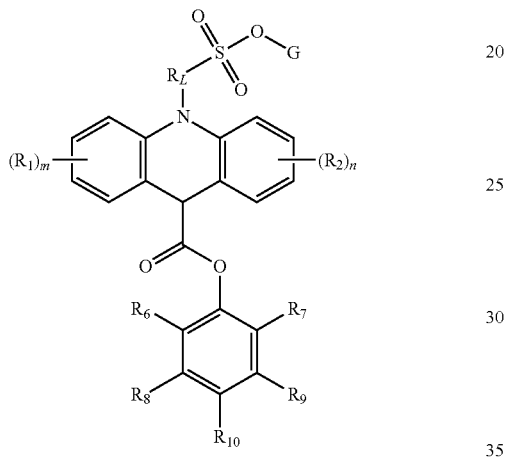

wherein $R_6$-$R_{10}$ are independently selected from hydrogen or a $C_1$-$C_{25}$ hydrocarbon radical optionally substituted with one or more heteroatoms, and wherein $R_6$-$R_{10}$ may optionally comprise a zwitterionic group and/or a zwitterionic linker group.

15. The N-alkylated acridan according to claim 14, wherein said N-alkylated acridan has the structure:

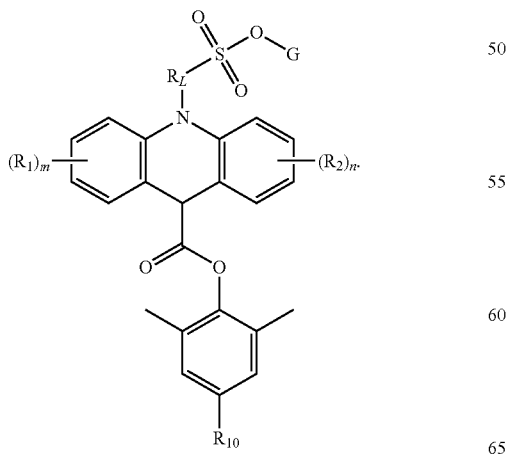

16. The N-alkylated acridan according to claim 13, wherein said N-alkylated acridan has the structure:

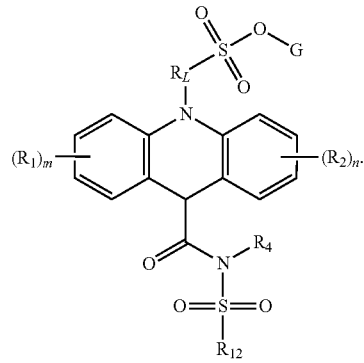

wherein $R_{12}$ is a $C_1$-$C_{20}$ hydrocarbon.

17. An N-alkylated acridinium having the structure:

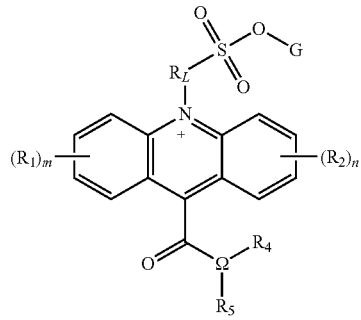

wherein G is an acid-labile protecting group;

"m" and "n" are independently 0-4 and at least one of "m" or "n" is greater than 0;

wherein Ω is O or N;

—$R_L$—is a $C_{1-20}$ linear or branched bivalent hydrocarbon radicals; optionally substituted with one or more heteroatoms, and combinations thereof, and wherein $R_L$ optionally comprises a zwitterionic linker group;

$R_1$ and $R_2$ are independently selected from electron donating groups;

$R_4$ is absent when $\Omega$ is O or hydrogen or a $C_1$-$C_{40}$ hydrocarbon radical optionally substituted with one or more heteroatoms, and wherein $R_4$ and $R_5$ may optionally comprise a zwitterionic group and/or a zwitterionic linker group; and $R_5$ hydrogen or a $C_1$-$C_{40}$ hydrocarbon radical optionally substituted with one or more heteroatoms, and combinations thereof and wherein $R_4$ and $R_5$ may optionally comprise a zwitterionic group and/or a zwitterionic linker group.

18. The N-alkylated acridinium according to claim 17, wherein said N-alkylated acridinium has the structure:

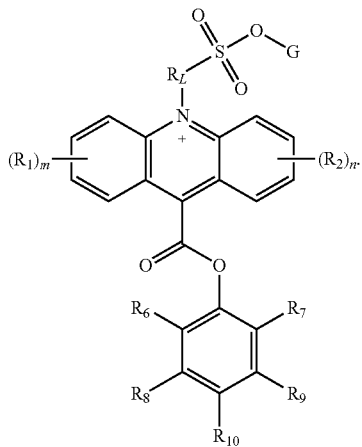

wherein $R_6$-$R_{10}$ are independently selected from hydrogen or a $C_1$-$C_{25}$ hydrocarbon radical optionally substituted with one or more heteroatoms, and wherein $R_6$-$R_{10}$ may optionally comprise a zwitterionic group and/or a zwitterionic linker group.

19. The N-alkylated acridinium according to claim 18, wherein said N-alkylated acridinium has the structure:

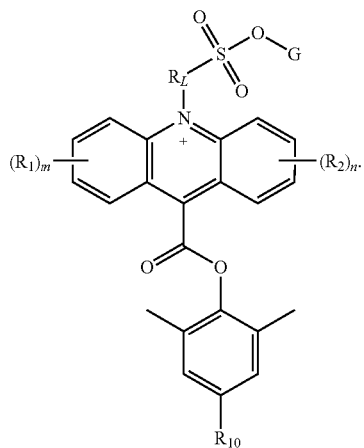

20. The N-alkylated acridinium according to claim 17, wherein said N-alkylated acridinium has the structure:

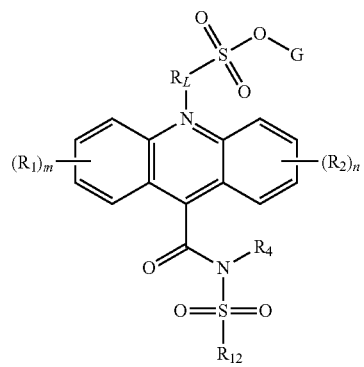

wherein $R_{12}$ is a $C_1$-$C_{20}$ hydrocarbon.

* * * * *